United States Patent
Ayoub et al.

(10) Patent No.: US 9,242,003 B2
(45) Date of Patent: Jan. 26, 2016

(54) SURFACE-MODIFIED HEAVY METAL NANOPARTICLES, COMPOSITIONS AND USES THEREOF

(71) Applicant: Metallo Therapy Ltd., Shefaram (IL)

(72) Inventors: Amal Ayoub, Maalot-Tarshiha (IL); Nassim Safadi, Nazareth (IL); Sobhi Basheer, Sakhnine (IL)

( * ) Notice: Subject to any disclaimer, the term of this patent is extended or adjusted under 35 U.S.C. 154(b) by 0 days.

(21) Appl. No.: 13/958,725

(22) Filed: Aug. 5, 2013

(65) Prior Publication Data

US 2014/0030345 A1    Jan. 30, 2014

Related U.S. Application Data

(63) Continuation of application No. PCT/IL2011/000854, filed on Nov. 3, 2011.

(60) Provisional application No. 61/439,004, filed on Feb. 3, 2011.

(51) Int. Cl.
| | |
|---|---|
| *A61K 9/16* | (2006.01) |
| *A61K 47/20* | (2006.01) |
| *B22F 1/00* | (2006.01) |
| *B22F 1/02* | (2006.01) |
| *B22F 9/24* | (2006.01) |
| *B82Y 30/00* | (2011.01) |
| *A61K 33/24* | (2006.01) |

(52) U.S. Cl.
CPC .................. *A61K 47/20* (2013.01); *A61K 33/24* (2013.01); *B22F 1/0022* (2013.01); *B22F 1/02* (2013.01); *B22F 9/24* (2013.01); *B82Y 30/00* (2013.01)

(58) Field of Classification Search
None
See application file for complete search history.

(56) References Cited

U.S. PATENT DOCUMENTS

| | | |
|---|---|---|
| 6,955,639 B2 | 10/2005 | Hainfeld et al. |
| 2002/0177143 A1 | 11/2002 | Mirkin et al. |
| 2004/0247924 A1 | 12/2004 | Andres et al. |
| 2006/0235087 A1 | 10/2006 | Alexandridis et al. |
| 2010/0284921 A1 | 11/2010 | Gordon et al. |
| 2011/0003343 A1 | 1/2011 | Nikiforov et al. |
| 2011/0300532 A1 | 12/2011 | Jahnen-Dechent et al. |

OTHER PUBLICATIONS

Brust et al., (1994) Synthesis of thiol-derivatised gold nanoparticles in a two-phase Liquid-Liquid system. J Chem Soc Chem Commun 7: 801-802.
Frens (1972) Particle size and sol stability in metal colloids. Colloid & Polymer Science 250 (7): 736-741.
Frens (1973) Controlled nucleation for the regulation of the particle size in monodisperse gold suspensions. Nature (London) Phys Sci 241: 20-22.
Kimling et al., (2006) Turkevich method for gold nanoparticle synthesis revisited. J Phys Chem B 110(32): 15700-7.
Manna et al., (2003) Optimized photoisomerization on gold nanoparticles capped by unsymmetrical azobenzene disulfides. Chem Mater 15(1): 20-28.
Martin et al., (2010) Charged gold nanoparticles in non-polar solvents: 10-min synthesis and 2D self-assembly. Langmuir 26(10): 7410-7.
Perrault and Chan (2009) Synthesis and surface modification of highly monodispersed, spherical gold nanoparticles of 50-200 nm. J Am Chem Soc 131(47): 17042-3.
Turkevich et al., (1951) a study of the nucleation and growth process in the synthesis of colloidal gold. Discuss Faraday Soc 11: 55-75.

*Primary Examiner* — Hasan Ahmed
(74) *Attorney, Agent, or Firm* — The Roy Gross Law Firm, LLC; Roy Gross

(57) ABSTRACT

Surface-modified heavy metal nanoparticles, including a heavy metal core and a coating layer, the coating layer having at least one ligand, conjugated to polyethylene glycol, the at least one ligand is selected from N-acetyl cysteine, albumin, cysteine, methionine, glutathione, amino thiols, thio-carboxylic acids, ammonia, amines, diamines or any combination thereof. Compositions including surface-modified heavy metal nanoparticles and uses thereof in treatment and diagnosis of various conditions.

22 Claims, 8 Drawing Sheets

SURFACE-MODIFIED HEAVY METAL NANOPARTICLES, COMPOSITIONS AND USES THEREOF

FIELD OF THE INVENTION

The invention relates to the field of surface modified metal nanoparticles and their use in treatment and diagnosis of various health related conditions.

BACKGROUND OF THE INVENTION

Nanoparticles are small object in a nano scale size, that behaves as a whole unit in terms of its transport and properties. Nanoparticles may exhibit size-related properties that differ significantly from those observed in fine particles or bulk materials. Methods for the preparation of gold nanoparticles have previously been reported (for example, J. Turkevich, et al., Discuss. Faraday. Soc. 1951, 11, 55-75; J. Kimling, et al, J. Phys. Chem. B 2006, 110, 15700-15707; G. Frens, Colloid & Polymer Science 1972, 250, 736-741; G. Frens, Nature (London), Phys. Sci. 1973, 241, 20-22; M. Brust et al., *J. Chem. Soc., Chem. Commun.* 1994, 7, 801-802; Manna, et al. (2003) *Chem. Mater.* 15 (1):20-28; S. D. Perrault; W. C. W. Chan (2009) *J. Am. Chem. Soc.* 131 (47): 17042; M. N. Martin et al., *Langmuir* 26 (10): 7410). Colloidal gold is often prepared by reduction of gold halides monodispersed particles with a diameter of 10±60 nm were described by Frens using sodium citrate for the reduction of $HAuCl_4$.

Gold hydrosol is a typical lyophobic colloid, the particles of which bears a large negative surface charge (the surface potential is ~50 mV) and, hence, it is stable only in very low-ionic-strength solutions. In lyophobic systems, the dispersion medium and the dispersed phase are substantially different in the chemical composition and the interface structure, as a result of which the surface forces at the interface are uncompensated. Therefore, these systems are thermodynamically unstable and require special stabilization.

Stabilizing gold nanoparticles: a strong negative charge of the gold particle surface provides their strong adsorption interactions with high-molecular-mass compounds. Sulfur and gold atoms are known to form dative bonds. Alkane thiol linkers $HS(CH2)nR(R=COOH, OH$ or $SO3H; n=11\pm22)$ are being used to achieve stronger attachment of bio-molecules to gold particles. Interactions of these linkers with gold afford thiolates which form a monolayer on the particle surface.

In recent years, synthetic polymers, such as polyethylene glycol (PEG), polyethyleneimine, polyvinylpyrrolidone, poly-(vinyl acetate), polyamidoamine (dendrimer), polydithiafulvene, chitosan, and the like, have found application in the synthesis of mono-dispersed colloidal gold (CG). Particles formed in the presence of these polymers are characterized by a higher size and shape uniformity. Unfortunately, the synthesis methods and stabilizers which have been used for producing stable gold nanoparticles did not provide the optimal gold nanoparticles for medical use, which needs highly stable and very concentrated metal nanoparticles in aqueous dispersion. Uses for metal nanoparticles in medical applications have been proposed, such as, for example, in U.S. Pat. No. 6,955,639, which is directed to methods of enhancing radiation effects with metal nanoparticles.

There still remains a need in the art for the preparation of metal nanoparticles that exhibit enhanced properties such as improved stability and solubility, reduced toxicity, enhanced bioavailability, improved pharmacokinetics, for their use in treatment and diagnosis of various health related conditions.

SUMMARY OF THE INVENTION

The present invention provides for novel surface-modified heavy metal nanoparticles, compositions comprising the same and uses thereof. The novel surface-modified heavy metal nanoparticles of the present invention exhibit improved properties as compared to other metal nanoparticle preparations. In particular, the present invention provides for novel polyethylene glycol (PEG)-N-acetyl cysteine (NAC) surface modified gold nanoparticles, which exhibit improved and enhanced properties. Further provided are methods for the preparation of the stable aqueous dispersion of surface-modified heavy metal nanoparticles which may be used for cancer treatment or cancer diagnosis.

In some embodiments, the present invention is based on the surprising and unexpected finding that metal nanoparticles modified by thiol containing groups such as Alkane thiol linkers $HS(CH2)_nR$ were found to be unstable in protein containing solutions, and other physiological solutions, as such that the nanoparticles form aggregates and lose their nanoparticulate form and structure. Unexpectedly, the inventors found that the novel composition of PEG-NAC, used for surface modification of metal nanoparticles enables the dispersion and solubility of such nanoparticles in protein containing solutions as well as other physiological solutions, such as, for example, blood and plasma. The use of NAC-PEG for surface modification provides superior results as compared to surface modification by thiol containing groups (such as NAC) alone, which do not allow the dispersion or solubility of nanoparticles in protein containing solutions and other physiological mediums. According to further embodiments, the novel PEG-NAC surface-modified heavy metal nanoparticles of the present invention exhibit improved/enhanced properties, such as, for example: improved solubility in water (i.e. being highly hydrophilic); improved stability (stable for a long period of over 6 months and stable at physiological conditions); reduced toxicity; improved bioavailability (lower does of the surface-modified heavy metal nanoparticles are needed to obtain a biological effect); improved pharmacokinetic properties (such as exemplified by higher half life in blood); being biodegradable; easy and cost effective to produce (even at larger industrial scale); and the like. In further embodiment, the improved properties of the novel surface-modified heavy metal nanoparticles allows the preparation of highly concentrated preparations of the coated heavy metal nanoparticles and further allows their production in the form of a powder. In further embodiments, the novel surface-modified heavy metal nanoparticles of the present invention allows the attachment of various drugs thereto, which may further be used as carriers to deliver drugs or other substances to a desired location. Thus, the novel surface-modified heavy metal nanoparticles of the present invention enable the use of higher amounts of the heavy metal, with a reduced toxicity and enhanced biological effect as compared to other metal containing nanoparticles.

Thus, in some embodiments, the present invention provides a surface-modified heavy metal nanoparticle, comprising a heavy metal core and a coating layer, the coating layer comprising at least one ligand, wherein the at least one ligand is bound to the surface of the heavy metal nanoparticle core and wherein the at least one ligand is conjugated to a polymer.

According to some embodiments there is provided a surface-modified heavy metal nanoparticle comprising: a heavy metal core and a coating layer, the coating layer comprising at least one ligand conjugated to polyethylene glycol (PEG), wherein the at least one ligand is selected from N-acetyl cysteine (NAC), albumin, cysteine, methionine, glutathione, amino thiols, thio-carboxylic acids, ammonia, amines, diamines or any combination thereof; and wherein the at least one ligand is bound to the surface of the heavy metal nanoparticle core. In some embodiments, the ligand is N-acetyl cysteine (NAC). In some embodiments, the at least one ligand is covalently bound to the surface of the heavy metal nanoparticle core.

In some embodiments, the heavy metal is selected from gold, gold species, silver, platinum, iron, copper, nickel, palladium, iridium, titanium or lead. In some embodiments, the heavy metal is gold species. In further embodiments, the gold species may be selected from $AuCl_3$, $AuF_3$, $AuBr_3$, $HAuCl_4$ or $MAuCl_4$, wherein M represents an alkali metal cation.

In further embodiments, the nanoparticle is of the size from about 0.5 nm to about 400 nm.

In some embodiments, the surface-modified heavy metal nanoparticles are in a substantially dry powder form.

In some embodiments, there is further provided an aqueous dispersion of the surface-modified heavy metal nanoparticles. The particles may be dispersed in water or in a buffer. In some embodiments, the buffer may be at a pH of between about 4.5 to about 8.

In some embodiments, there is provided a surface-modified gold nanoparticle comprising: a gold species metal core and a coating layer, the coating layer comprising N-acetyl cysteine (NAC) ligand conjugated to polyethylene glycol (PEG), wherein the N-acetyl cysteine (NAC) ligand is bound to the surface of the gold species nanoparticle core.

According to some embodiments, there is provided a composition comprising N-acetyl cysteine (NAC) conjugated to polyethylene glycol (PEG), for the surface modification of metal nanoparticles.

According to some embodiments, there is provided a process for the preparation of surface-modified heavy metal nanoparticles comprising the steps of:
adding at least one ligand conjugated to poly ethylene glycol (PEG) to a mixture comprising metal nanoparticles, wherein the at least one ligand binds to the surface of the heavy metal nanoparticles core, yielding surface-modified heavy metal nanoparticle, wherein the ligand ligand is selected from N-acetyl cysteine (NAC), albumin, cysteine, methionine, glutathione, amino thiols, thio-carboxylic acids, ammonia, amines, diamines or any combination thereof. In some embodiments, the ligand is N-acetyl cysteine (NAC). In some embodiments, the mixture is prepared by:
mixing at least one surfactant with at least one organic solvent in a water solution to yield an emulsion; and
adding to the emulsion of step (a) a solution of heavy metal species and at least one reducing agent, to yield reduced metal nanoparticles.

In some embodiments, the heavy metal is a gold species, selected from AuCl3, AuF3, AuBr3, HAuCl4 or MAuCl4, wherein M represents an alkali metal cation. In some embodiments, the heavy metal nanoparticles are of a size of from about 0.5 to about 400 nm.

In some embodiments, the process further comprises drying the aqueous phase, yielding surface-modified heavy metal nanoparticles in a dry form.

In some embodiments, the process comprises dispersing the heavy metal nanoparticles in water or in a buffer. The buffer may be at a pH between about 4.5 to about 8.

In some embodiments, the at least one surfactant comprises at least one fatty acid. In some embodiments, the at least one fatty acid is oleic acid.

In some embodiments the organic solvent is ethanol. In some embodiments the at least one reducing agent is any one of ascorbic acid, ethylene diamine tetraacetic acid (EDTA), sodium citrate, sodium borohydride or lithium borohydride. In some embodiments, the reducing agent is ascorbic acid.

In some embodiments, the process further comprises adding at least one second organic solvent. In some embodiments, the second organic solvent is selected from hexane, cyclohexane, chloroform, diethyl ether, ethyl acetate and toluene. In some embodiments, In some embodiments, there is provided a pharmaceutical composition comprising the surface-modified heavy metal nanoparticles. The pharmaceutical composition may further comprise at least one of pharmaceutically acceptable additives, carriers, buffers, stabilizers or excipients. In some embodiments, the pharmaceutical composition is suitable for oral administration, injection or infusion. In some embodiments, the pharmaceutical composition is for use in medical treatment or medical diagnosis. In some embodiments, the pharmaceutical composition is for use in the treatment of diagnosis of malignant disorders, wherein the malignant disorder is any one of carcinoma, sarcoma, germ cell tumors or blastoma. In further embodiments, the treatment or diagnosis is in vitro or in vivo.

In additional embodiments, there is provided an injectable solution comprising the pharmaceutical composition, which comprises the surface-modified heavy metal nanoparticles. In further embodiments, there is provided a sterile syringe comprising the injectable solution.

In some embodiments, there is provided a kit comprising an aqueous dispersion of the surface-modified heavy metal nanoparticles. In some embodiments, the dispersion comprises water or a buffer at pH values of between about 4.5 to about 8, or pharmaceutical composition comprising the same; means for administering the aqueous dispersion or pharmaceutical composition into a patient; and instructions for use.

In some embodiments, there is provided a kit comprising the surface-modified heavy metal nanoparticles in a dry form; an aqueous solution for dispersing the surface-modified heavy metal nanoparticles. In some embodiments, the dispersion comprises water or a buffer at pH values of between 4.5 and 8; means for administering the aqueous dispersion into a patient; and instructions for use.

In further embodiments, there is provided a method of treatment or diagnosis of a malignant disorder comprising the steps of administrating a subject in need a therapeutically effective amount of the surface-modified heavy metal nanoparticles or of a pharmaceutically composition comprising the same. The administration may be performed by oral, infusion or injection administration routes.

In additional embodiments, there is provided an N-acetyl cysteine (NAC)-polyethylene glycol (PEG) conjugate for use in surface modification of metal nanoparticles, wherein the N-acetyl cysteine (NAC) is capable of bounding to the surface of the metal nanoparticle core. In some embodiments, the metal is gold species.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 3A—change in body weight of group I mice (treated with 100 mg/kg gold nanoparticles every other day, for six days). FIG. 3B—change in body weight of group II mice (treated with 100 mg/kg gold nanoparticles, iv, for five days, two days off and 5 more days (5/2/5)). FIG. 3C—change in body weight of group III mice (treated with 150 mg/kg gold nanoparticles, iv, 5/2/5). FIG. 3D—change in body weight of group IV mice (treated with 200 mg/kg gold nanoparticles, iv, 5/2/5). No mortality occurred in the animals treated with the GNPs prior to the scheduled termination, carried out 26 days post-dosing;

DETAILED DESCRIPTION OF THE INVENTION

Figure 1A:
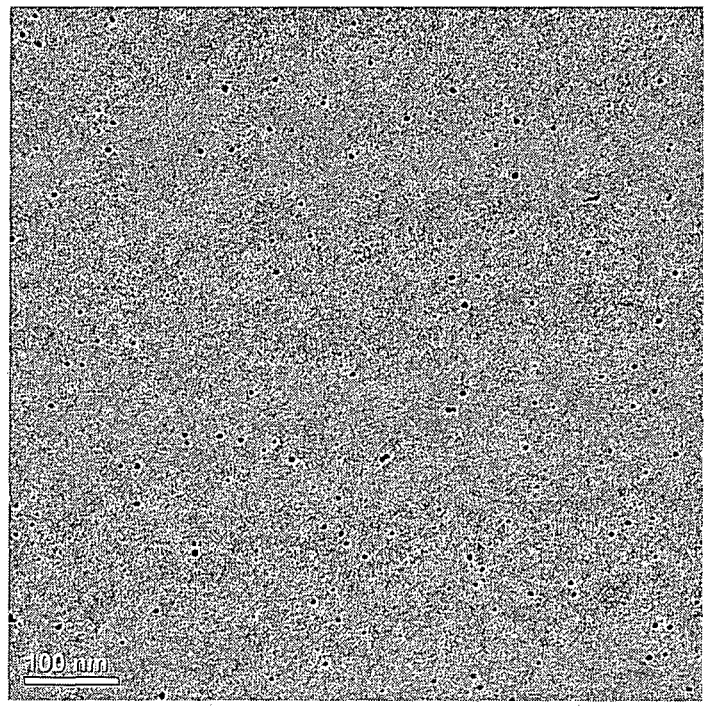
FIGS. 1A-1B are Transmission Electron Microscopy (TEM) images showing a field of an aqueous dispersion of surface coated gold nanoparticles as indicated by the appearance of black dots at a magnification of 100 nm (FIG. 1A) and 50 nm (FIG. 1B). The images indicate that the nanoparticles are separate and have a size smaller than or equal to 10 nm.

The present disclosure is based on results of a research that surprisingly provides stable and non-toxic aqueous dispersions of surface modified heavy metal nanoparticles, present at high concentration in the aqueous dispersions, which may be systemically administered to a subject and may exhibit improved properties, such as, reduced toxicity, improved stability, enhanced bioavailability, improved pharmacokinetics, and the like.

The inventors have developed a novel aqueous dispersion of surface-modified metal nanoparticles and a methodology allowing their preparation. In particular, the inventors have developed novel surface-modified gold nanoparticles, wherein the surface modification comprises N-acetyl cysteine (NAC) ligand conjugated to polyethylene glycol (PEG), wherein the N-acetyl cysteine (NAC) ligand is bound to the surface of the gold species nanoparticle core. Unexpectedly, such modification provides improved and enhanced properties to the nanoparticles. As exemplified herein, the improved properties include such properties as, but not limited to: improved solubility in water (i.e. being highly hydrophilic); improved stability (stable for a long period of over 6 months and stable at physiological conditions); reduced toxicity; improved bioavailability (lower does of the surface-modified heavy metal nanoparticles are needed to obtain a biological effect); improved pharmacokinetic properties (such as exemplified by higher half life in blood); being biodegradable; easy and cost effective to produce (even at larger industrial scale); and the like.

The inventors have found that the formation of a stable aqueous dispersion of surface-modified gold nanoparticles is possible by preparing an intermediate-state compound, namely reduced gold nanoparticles in an emulsion environment, prior to the addition of a coating ligand thereby obtaining surface-modified gold nanoparticles. The preparation of the aqueous dispersions of gold nanoparticles via the above mentioned intermediate step assists in obtaining stable gold nanoparticles which can be stably dispersed in aqueous solutions, particularly at significant concentrations.

The surface-modified metal nanoparticles disclosed herein are present in the aqueous dispersions of the invention at high concentrations and are stable at physiological pH of 7.3-7.4 or in a living cell, tissue, organ, and in in vivo or in in vitro environments. In addition, the nanoparticles may be used by systemic administration as therapeutic means or for diagnostic purposes.

For example, the aqueous dispersions of the surface-modified metal nanoparticles contained at high concentrations, may significantly improve the radiation therapy of malignant disorders possibly by the ability of the gold nanoparticles to absorb significantly more of the treatment radiation than other light atoms surrounding them and their ability to emit secondary radiation in the form of electrons and low energy photons, this secondary radiation being highly effective in destroying cancer cells.

The aqueous dispersions of surface-modified gold nanoparticles are produced by novel preparation methods as described below.

The present invention encompasses several aspects as will be described below, and may be summarized as follows: surface-modified metal nanoparticles, an aqueous dispersion of surface-modified metal nanoparticles, a method for their preparation, pharmaceutical compositions comprising the same and their uses in medical treatment or diagnosis.

Thus, in accordance with one aspect, there is provided surface-modified heavy metal nanoparticle, comprising a heavy metal core and a coating layer, the coating layer comprising at least one ligand, wherein the at least one ligand is bound to the surface of the heavy metal nanoparticle core through covalent bonds.

The term "nanoparticle" is used herein to denote any microscopic particle smaller than about 400 nm in diameter, wherein each nanoparticle behaves as a complete unit in terms of the transport characteristics and physical and chemical properties.

As used herein the term "about" refers to ±10% of the indicated value.

The term "heavy metal" is used herein to denote a member of a subset of elements that exhibit metallic properties, which may include transition metals, metalloids, lanthanides, or actinides.

In some embodiments, the heavy metal may be for example any one of gold, platinum, silver, iron, copper, nickel, palladium, iridium, titanium or any other heavy metal. According to one embodiment, the metal is iron.

According to some embodiments, the metal is gold. According to further embodiments, the gold is a gold species selected from AuCl3, AuF3, AuBr3, HAuCl4 or MAuCl4, wherein M represents an alkali metal cation.

As used herein the term "surface-modified heavy metal nanoparticles" refers to metal nanoparticles, comprising a coating layer on their surface, whereby the coating layer modifies the nanoparticles surface and wherein the coating layer comprises at least one ligand. In some embodiments, the ligand may be further conjugated to a polymer.

As used herein the term "PEG-NAC surface modified heavy metal nanoparticles" is directed to heavy metal core nanoparticle and a coating layer, the coating layer comprising N-acetyl cysteine (NAC) ligand conjugated to polyethylene glycol (PEG), wherein the N-acetyl cysteine (NAC) ligand is bound (covalently or non covalently) to the surface of the heavy metal nanoparticle core. In exemplary embodiments, the heavy metal is a gold species.

As used herein, the terms "PEG-NAC compound(s)", "PEG-NAC conjugate(s)" or "PEG-NAC molecule(s)" may interchangeably be used and are directed to a compound comprising polyethylene glycol (PEG) conjugated to N-acetyl cysteine (NAC).

As used herein the term "NAC surface modified heavy metal nanoparticles" is directed to heavy metal core nanoparticle and a coating layer, comprising N-acetyl cysteine (NAC) ligand, which is not conjugated to polyethylene glycol (PEG). The N-acetyl cysteine (NAC) ligand is bound (covalently or non covalently) to the surface of the heavy metal nanoparticle core. In exemplary embodiments, the heavy metal is a gold species.

As used herein, the term "GNP(s)" is directed to gold nanoparticles.

As used herein the coating of the nanoparticles surface with the at least one ligand is for example coating at least 60%, at least 70%, at least 80%, at least 90% of the outer surface of the core of the nanoparticle.

The term "ligand" as used herein is any organic ligand which is soluble in water and is capable of binding (covalently or non-covalently) the surface of the metal nanoparticles core and thus modifying the surface of the nanoparticles by coating the surface, thereby forming surface-modified metal nanoparticles.

In some embodiments, the ligand is at least one of N-acetyl cysteine, albumin, or amino acids such as for example, but not limited to cysteine, methionine and glutathione, amino thiols, thio-carboxylic acids, ammonia and amines, diamines or any combination thereof, or any ligand capable of binding gold nanoparticles.

In one embodiment, the ligand may be N-acetyl cysteine. In one embodiment, the ligand may be cysteine.

In accordance with the present disclosure, the ligand may have at least one free thiol group which may bind for example to the metal nanoparticles via the interaction of the any one of the thiol groups of the ligand and the metal atoms.

According to some embodiments, the ligand may be conjugated to a polymer. In one embodiment, the polymer is polyethylene glycol (PEG).

According to one embodiment, the surface-modified metal nanoparticles are of a size of from about 0.5 nm to about 400 nm.

In some embodiments, the size is smaller than 100 nm, for example smaller than 90 nm, smaller than 80 nm, smaller than 70 nm, smaller than 60 nm, smaller than 50 nm, smaller than 40 nm, smaller than 30 nm, smaller than 20 nm, or smaller than 10 nm. In some embodiments, the nanoparticles are of a size smaller than 10 nm.

In some embodiments, the surface-modified heavy metal nanoparticle may be in a substantially dry powder form. The dry powder may be stored under appropriate conditions for example under vacuum conditions at temperatures of between about 2° C. to about 8° C. for long periods of time, possibly until further use.

In some embodiments, the present invention provides an aqueous dispersion of surface-modified heavy metal nanoparticles, dispersed in water or in a buffer at pH between about 4.5 to about 8, for example, in a physiological buffer at pH between about 7.3 to about 7.4.

According to some embodiments, an aqueous dispersion of surface-modified heavy metal nanoparticles may be obtained by dissolving the dry powder comprising the surface-modified heavy metal nanoparticle, in water or in a buffer solution at a pH between about 4.5 to about 8, for example, at physiological pH of about 7.3 to about 7.4.

The surface-modified nanoparticles dispersions of the invention are chemically as well as physically storage-stable for at least 3 month, and even for a period of 6 months, when stored at appropriate storage conditions of 2° C.-8° C.

The "stability" in the context of the present disclosure may be determined by various chemical and/or physical methods, and is to be taken to mean that no significant formation of aggregates or precipitation are observed. Under these storage conditions, no formation of aggregates or precipitation is observed. In some embodiments, "stability" is directed to the preservation of the nano size of the particles.

In general, it can be appreciated that the stabilization depends on solubility of the ligand in a dispersion medium, the ability of nanoparticles to bind the ligand on their surface and the degree of the surface coverage by the ligand.

The aqueous dispersions of surface-modified metal nanoparticles of the present invention may be used in cancer treatment. As shown in the exemplary embodiments, when cancer cells were incubated in medium comprising the aqueous dispersions of gold nanoparticles, the gold nanoparticles were delivered into cancer cells in an amount which is dependent on the nanoparticles concentration in the incubation medium and on the incubation time, with no observed toxicity side effects.

The present disclosure provides the method for the preparation of surface-modified heavy metal nanoparticle comprising the steps of:
(a) mixing at least one surfactant with at least one organic solvent in a water solution to yield an emulsion;
(b) adding to the emulsion of step (a) a solution of heavy metal species and at least one reducing agent, to yield reduced metal nanoparticles;
(c) adding at least one ligand to the mixture of step (b), wherein the at least one ligand binds the surface of the heavy metal nanoparticles core, yielding surface-modified heavy metal nanoparticle.

The method may further include an additional step (d) which comprises separating the inorganic phase which contains the heavy metal nanoparticles from the organic phase.

In some embodiments, the at least one organic solvent of step (a) is a water miscible organic solvent. In some embodiments, step (a) the at least one surfactant is mixed with at least one first water-miscible organic solvent in a water solution to yield an emulsion.

The term "surface-modified heavy metal nanoparticle" is directed to heavy metal nanoparticles coated with a ligand, wherein the ligand is bound to the surface of the metal nanoparticles, thereby modifying said surface, and wherein the "heavy metal" may be any one of gold, platinum, silver, iron, copper, nickel, palladium, iridium, titanium or any other heavy metal. In one embodiment, the metal is gold. In some embodiments, the ligand may be further conjugated to another substance, such as a polymer.

In accordance with the first step of the process (a), an emulsion is obtained upon mixing at least one surfactant with at least one first water-miscible organic solvent in an alkaline base or water solution.

The term "emulsion" is to be understood in the context of the present invention as a mixture of two or more immiscible (unblendable) liquids. Emulsions are made up of a dispersed and a continuous phase; the boundary between these phases is called the interface. Microemulsions tend to appear clear due to the small size of the disperse phase.

In the context of this invention, the term "surfactant" may be referred to a compound that lowers the surface tension of a liquid.

In some embodiments, the surfactant may comprise a fatty acid, wherein the fatty acid may be for example a long-chain saturated fatty acid or a mono- or poly-unsaturated fatty acid.

In some embodiments, the fatty acid may be selected for example from oleic acid, linoleic acid or erucic acid, palmitoleic acid, sapienic acid myristoleic acid. According to some embodiments the fatty acid is oleic acid According to some embodiments, the at least one surfactant may comprise a mixture of fatty acids. According to some other embodiments, the mixture of fatty acids may predominantly comprise oleic acid. In some specific embodiments the mixture of fatty acids comprises 65% wt. of oleic acid.

In the context of this invention, the at least one "first water-miscible organic solvent" is to be referred to any organic solvent which upon mixing with water forms a substantially uniform mixture. The water-miscible organic solvent according to the invention may be ethanol or acetone. According to some embodiments, the water-miscible organic solvent may be ethanol.

The term "an alkaline solution" in the context of the present invention is to be referred to a as a solution of a soluble base, wherein "base" is defined by the general chemistry definition, wherein a base is a substance that can accept hydronium ions.

The base used according to the present invention may be any alkaline base for example sodium hydroxide solution or potassium hydroxide solution or any other alkaline metal hydroxide but other bases may be also suitable including for example ammonia. In some embodiments, the base is sodium hydroxide.

The solution comprising the at least one surfactant, wherein the surfactant may be for example fatty acid or a mixture of fatty acids, at least one first water-miscible organic solvent may be mixed in an alkaline solution to form an emulsion under conditions which partially dissolve the fatty acids.

Mixing may be for example using a magnetic stirrer for a suitable amount of time for example for about 5 minutes at a temperature such as room temperature.

In accordance with the second step of the process (b), a solution of heavy metal species and at least one reducing agent are added to the emulsion detailed above to yield reduced metal nanoparticles.

In some embodiments, the "heavy metal" may be any metal species as defined and detailed above. In some embodiments, the metal is gold.

The "ionic metal species" as used herein is considered to be any substance or chemical entity that contains or can generate (and therefore a precursor) metal ions According to some embodiments wherein the metal is gold, "ionic gold species" may be selected from $AuCl_3$, $AuF_3$, $AuBr_3$, $HAuCl_4$ or $MAuCl_4$, wherein M represents an alkali metal cation, for example sodium or potassium cation. According to some other embodiments, the ionic gold species is $HAuCl_4$. $HAuCl_4$ is thus a precursor ionic species, which yields $[AuCl_3]$-ions.

According to some other embodiments "ionic metal species" may be selected from $FeCl_2$, $FeSO_4$, $FeCl_3$.

The at least one "reducing agent" used herein is an agent capable of reducing the ionic metal species within the emulsion. In some embodiments, the reducing agent is organic or inorganic. Non-limiting examples of such reducing agents may be for example any one of ascorbic acid, ethylene diamine tetraacetic acid (EDTA), sodium citrate in the presence or absence of tannin, sodium borohydride, borohydride in a mixture with sodium citrate or EDTA and cyanoborohydride, hydrazine, sodium diphenylaminosulfonate or lithium borohydride and any combinations thereof.

According to some other embodiments, the reducing agent is ascorbic acid.

In an embodiment where the metal is gold, the reducing agent may be added for example at a 2:1 molar ratio relative to the ionic gold species.

Alternative reducing methods which may be used in accordance with the present invention may be for example irradiation methods such as ultrasonic, UV irradiation or pulse or laser radiolysis.

In an embodiment where the metal is gold, the ionic metal species may be added during mixing, and may optionally result in a yellowish solution. Upon addition of a solution comprising the at least one reducing agent, the solution color may change to red-wine purple color, possibly indicating completion of the reduction of the ionic gold species.

In the context of the present application, it is to be understood that addition of metal species within the emulsion may provide means to control the size of the formed nanoparticles and hence enables the formation of nanoparticles of a predetermined size.

In accordance with the third step of the process (c), at least one ligand is added to the mixture above.

The term "ligand" as used herein is as detailed above and may be any organic ligand which is soluble in water and is capable of coating the surface of the metal nanoparticles by binding (covalently or non-covalently) to the metal thereby forming surface-modified metal nanoparticles.

The covalent binding of the at least one ligand having at least one free thiol group may be for example via the interaction of the any one of the thiol groups of the ligand and the metal atoms.

In some embodiments, the ligand is at least one of N-acetyl cysteine, albumin and amino acids, for example cysteine and methionine, glutathione, amino thiols, thio-carboxylic acids, ammonia and amines, diamines or any combinations thereof or any ligand capable of binding metal nanoparticles.

In some embodiments, the ligand is N-acetyl cysteine. In some embodiments, the ligand is cysteine. The molar ratio between the metal and the ligand may be 1:4, preferably 1:6, more preferably 1:8.

In accordance with the invention, the ligand may be conjugated to a polymer. The polymer according to the present disclosure is an inert and a nontoxic polymer. Polymers typically used as include, without being limited thereto: polyethylene glycol (PEG), polyethyleneimine, polyvinylpyrrolidone, poly-(vinyl acetate), polyamidoamine (dendrimer), polydithiafulvene, chitosan.

In some embodiments, the polymer may be a linear polymer, for example PEG.

According to the present disclosure, conjugation of PEG to the at least one ligand may be performed before the addition of the at least one ligand to the mixture as detailed above.

According to some embodiments, the surface modification of the metal nanoparticles is a compound of N-acetyl cysteine (NAC) conjugated to polyethylene glycol (PEG). In some embodiments, the molar ratio between the metal nanoparticles and NAC-PEG compound may be at the range of about 1:1 to 1:20. For example, in some embodiments, the molar ratio between the metal nanoparticles and NAC-PEG compound may be 1:1. For example, in some embodiments, the molar ratio between the metal nanoparticles and NAC-PEG compound may be 1:2. For example, in some embodiments, the molar ratio between the metal nanoparticles and NAC-PEG compound may be 1:4. For example, in some embodiments, the molar ratio between the metal nanoparticles and NAC-PEG compound may be 1:8. For example, in some embodiments, the molar ratio between the metal nanoparticles and NAC-PEG compound may be 1:10. For example, in some embodiments, the molar ratio between the metal nanoparticles and NAC-PEG compound may be 1:20.

According to some embodiments, there is provided a NAC-PEG compound. In some embodiments, the NAC-PEG compounds may be used for the surface modification of metal nanoparticles.

In accordance with the present invention, the aqueous dispersion of surface-modified heavy metal nanoparticles may be conjugated to a second molecule for example to an antibody, wherein the antibody may assist in targeting the metal nanoparticles for example to a site of interest as for example in diagnosis. In addition, the nanoparticles of the present invention may be conjugated to a visually or otherwise detectable moiety, for example a chromophore or fluorophore.

Following the addition of the at least one ligand, the solution may be mixed for a suitable periods of time for example but not limited to about 30 minutes, more preferably for more than an hour.

The addition of the at least one ligand to the mixture comprising reduced metal nanoparticles may result in the formation of water-soluble surface-modified metal nanoparticles.

According to some embodiments, the pH may be adjusted during the addition of the at least one ligand to a basic pH, preferably to a pH value above pH of 9, 9.5, 10, preferably above pH 9. This may allow most of the fatty acid to be converted to fatty acid salt, which in turn allows the ligand to bind the gold nanoparticles.

The pH may be adjusted according to the invention using for example by titration with any alkaline base, possibly sodium hydroxide or potassium hydroxide.

According to some further embodiments, at least one second organic solvent may be added to the solution comprising water-soluble surface-modified gold nanoparticles and the pH may be thereafter adjusted to an acidic pH. The solution may be stirred for example for at least an hour.

According to the present invention, the "second organic solvent" is any organic solvent which is immiscible with water which at an acidic pH dissolves the fatty acid. The addition of this solvent tends to cause separation of the two phases into un-emulsified distinct phases, thereby separating the organic phase from the aqueous phase.

In some embodiments, the second organic solvent is hexane, cyclohexane, diethyl ether, pentane, cyclopentane, chloroform, ethyl acetate or toluene. According to some embodiment, the second organic solvent is hexane.

According to some embodiments, the second organic solvent is added and the pH is adjusted to an acidic pH, for example, lower than pH 7, lower than pH 6.5, lower than pH 6, lower than pH 5.5, lower than pH 5, lower than pH 4.5, lower than pH 4, lower than pH 3. In some embodiments, the pH is lower than pH 6.5. The pH may be adjusted using any acid, for example HCl.

The addition of a second organic solvent and adjusting the pH to an acidic pH enables the phase separation, wherein the emulsion is separated into an aqueous phase and an organic phase.

The aqueous phase may comprise the surface-coated metal nanoparticles, wherein the organic phase may comprise the organic solvents and fatty acids.

According to some embodiments, the at least one ligand may be also added to the reaction mixture following the addition of the second organic solvent. According to some embodiments, the at least one ligand will bind free sites on the surface of the metal nanoparticles. According to this embodiment, the ligand may be, for example, albumin that may be added and the mixture may be allowed to stir, for example, for 30 min on a magnetic stirrer.

Following the phase separation, the organic phase may be separated from the aqueous phase for example by suitable means, such as, for example by using a separation funnel.

In accordance with the present invention, the aqueous phase may be further dried. Drying of the aqueous phase according to the present invention may be, for example, by evaporation, vacuum drying, freeze-drying (lyophilization), desiccation or any other suitable technique of removing water residues or moisture and obtaining a product which is solid, for example, in a powder form.

In some embodiments, drying may comprise evaporation of traces of the first water-miscible organic solvent, resulting in a dried powder of surface-modified metal nanoparticles.

In some embodiments, the dry powder may be dissolved in water or in a buffer solution at a pH between about 4.5 to about 8, preferably at physiological pH of 7.3-7.4. Dissolving the dry powder yields an aqueous dispersion of surface-modified heavy metal nanoparticles.

In some embodiments, the aqueous dispersion of metal nanoparticles comprises metal nanoparticles at the size of from about 1 nm to about 100 nm, from about 1 nm to 10 nm, from about 10 nm to 20 nm, from about 20 nm to 30 nm, from about 30 nm to 40 nm, from about 40 nm to 50 nm, from about 50 nm to 60 nm, from about 60 nm to 70 nm, from about 70 nm to 80 nm, from about 80 nm to 90 nm, from about 90 nm to 100 nm. In some embodiments, the metal nanoparticles are of a size smaller than 10 nm.

The metal nanoparticles of the present invention are dispersed in an aqueous solution at concentrations of 0.001 µM-1M, for example at concentrations greater than 0.005M, greater than 0.01 M, greater than 0.05M, greater than 0.1 or sometimes greater than 0.5M.

Preparation of metal nanoparticles may be performed by using the two-phase micro emulsion method (for example as described by M. Burst et al., J. Chem. Soc., Chem. Commun. S, 1994, 7, 801-802). Accordingly, metal-containing reagents are transferred from an aqueous to an organic phase. After the addition of a surfactant solution, a micro emulsion is formed. The reduction reaction proceeds in a dispersed phase in which the drop size is at most 100 nm. As a result, virtually mono dispersed nanoparticles are formed. In micro emulsion methods of synthesis of nanoparticles, alkane thiols are often added to the reaction solution, for the stabilization of the particles. The final gold nanoparticles are dispersed in organic phase, stabilized with alkane thiol.

In another aspect, the present invention provides a pharmaceutical composition comprising surface-modified heavy metal nanoparticles as disclosed herein. In some embodiments, the pharmaceutical composition and formulations may include sterile aqueous solutions which may also comprise at least one of pharmaceutically acceptable additives such as, but not limited to, penetration enhancers, carrier compounds, buffers, stabilizers, diluents or other pharmaceutically acceptable carriers or excipients.

According to some embodiments, the pharmaceutical composition may be used in medical treatment or in medical diagnosis.

The pharmaceutical compositions of the present disclosure may be used for example in the medical diagnosis of malignant disorders. "Medical diagnosis" as used herein refers to the determination of the identity of a possible disease or disorder. Diagnosis may be based on combinations of signs, symptoms and test results. In accordance with the present disclosure, the pharmaceutical composition may be used for example in cancer detection for example as probes for molecular imaging, photoactive agents for optical imaging, contrast enhanced agent in computer tomography (CT) or in magnetic resonance imaging (MRI) or any method capable detecting cancer and providing evaluation thereto.

The pharmaceutical compositions of the invention may also comprise additional therapeutically active agents.

According to some embodiments, the pharmaceutical composition may be suitable for oral administration, injection or infusion.

The pharmaceutical compositions of the present disclosure may be used, for example, in the treatment of malignant disorders or cell proliferative disorders, such as, for example malignancies, that may be, for example solid or non-solid tumors. In some embodiments, the pharmaceutical compositions of the present disclosure may be used, for example, in the treatment of non-malignant disorders associated with increased, enhanced or abnormal proliferation of cells.

In some embodiments, the malignant disorders may be, for example, solid tumors such as carcinoma, sarcoma, melanoma, germ cell tumors or blastoma.

In some embodiments, the malignant disorders may be for example tumors in lip and oral cavity, pharynx, larynx, paranasal sinuses, major salivary glands, thyroid gland, esophagus, stomach, small intestine, colon, colorectum, anal canal, liver, gallbladder, extrahepatic bile ducts, ampulla of Vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

In some embodiments, the malignant disorders may comprise, for example, non-solid tumors such as leukemia or lymphomas.

In some embodiments, the medical treatment may be, for example, radiation therapy of malignant disorders or any treatment in combination with radiation therapy. Accordingly, pharmaceutical composition comprising the aqueous dispersion of metal nanoparticles may be used in radiation therapy to enhance the selectivity in treatment of malignant disorders.

Radiation therapy is to be understood as a therapy that uses high energy radiation sources such as but not limited to X-rays, gamma rays, and charged particles for cancer treatment by affecting the cancer cells viability.

The radiation may be delivered by an external beam radiation source apparatus, synchrotron radiation sources, or alternatively by an internal radiation source such as a radioactive material delivered within the body to a location which is in close proximity to the cancer cells, such as brachytherapy.

In other embodiments, the pharmaceutical composition of the invention may be used in combination with any hyperthermia treatment for example in combination with laser, UV, RF, ultrasound and any other source of hyperthermia used.

It is to be understood that the aqueous dispersion of surface-modified metal nanoparticles may be themselves used in therapeutically for medical treatment or medical diagnosis or alternatively in combination with radiation or in combination with any treatment method conventionally used.

According to some embodiments, the pharmaceutical composition may be administered to a patient, for example, by systemic administration or topical administration.

The term "systemic administration" is to be referred as a route of administration comprising enteral administration comprising for example oral, rectal, sublingual or buccal administration or parental administration which may comprise for example piercing the skin or mucous membrane.

The term "topical administration" is to be referred as a route of administration comprising application to the surface of a body part.

In some embodiments, the route of administration may involve, for example, intravenous (i.v.), intramuscular (i.m.), intraperitoneal (i.p.), transdermal, transmucosal, intra-tumor, intragastric, intranasal or orally for example by tablets, capsules, lozenges or drops, or topical administration for example by creams, dermal patches and the like or any combination thereof.

In some embodiments, the pharmaceutical composition may be delivered to the circulation through the digestive system, via intragastric or oral administration.

In some embodiments, the pharmaceutical composition may be administrated by injection or infusion.

In some embodiments, the pharmaceutical composition may be administered directly to the target of interest, for example, for use in radiation therapy. In some embodiments, the administration may be in close proximity to the tumor to be treated, for example, by injection.

It is to be understood that the aqueous dispersion of surface-modified metal nanoparticles may be administered themselves as described above for the pharmaceutical composition.

As can be understood herein the treatment as described according to the present invention may be achieved by using an effective amount of the aqueous dispersion of surface-modified metal nanoparticles or compositions comprising the same.

The terms "effective amount", "therapeutically effective amount" or "dosing" are used herein interchangeably and mean any amount necessary to achieve a selected result, which present may involve the amount of metal nanoparticles necessary for treating cancer or proliferative malignant or non-malignant disorders, specifically, killing the cancerous or otherwise abnormal cells.

The therapeutic effective amount, or dosing, is dependent on severity and responsiveness of the disease state to be treated, with the course of treatment lasting one hour to several hours, or until a cure is effected or a diminution of the disease state is achieved. Dosing may be provided to a person in need in a regimen comprising dosing of one daily or multiple daily administrations.

Persons of ordinary skill can readily determine optimum dosages, dosing methodologies and repetition rates. Optimum dosages may vary depending on the relative potency of the aqueous dispersion of the surface-modified gold nanoparticles of the invention, or compositions comprising thereof, and can generally be estimated based on EC50, found to be effective in in vitro cellular models, ex vivo organ or tissue model as well as in in vivo animal models. Persons of ordinary skill in the art can easily estimate repetition rates for dosing based on measured residence times, concentrations which may be affected for example by age, sex and weight of the subject in need.

In accordance with the present disclosure, when used in a combination therapy, dosing may be adjusted accordingly, for example radiation therapy or any additional therapy used.

The terms "disease", "disorder" and "condition" are used herein interchangeably.

As used herein to describe the present invention, "malignant", "cancer", "tumor", "malignancy", "proliferative malignant", "hyperproliferative" all relate equivalently to a hyperplasia of a tissue or an organ.

The terms "treat", "treating" or "treatment" as used herein means ameliorating one or more clinical indicia of disease activity in vivo in a patient having cancer or a proliferative malignant or non-malignant disease. "Treatment" refers herein to therapeutic treatment.

In some embodiments, treatment or diagnosis of malignant disorders using the aqueous dispersion of surface-modified metal nanoparticles or pharmaceutical composition comprising the same may be performed in vitro or in vivo.

As used herein, the term "in vivo" may refer to an in vivo treatment or in vivo diagnosis and is to be understood as a process that takes place within a living organism. The term in vivo when referring to diagnosis in vivo is also to be understood as any diagnosis which may be performed in an invasive or in a noninvasive manner such as but not limited to MRI, CT in a living organism.

The term "in vitro" encompasses any treatment or diagnosis which is performed on a body fluid such as, blood, urine, saliva or cerebrospinal fluid (CSF), organ, or tissue which can be extracted from a patient in need.

In another aspect of the present invention, there is provided a use of the surface-modified heavy metal nanoparticles as described above in the preparation of a pharmaceutical composition.

In some embodiments, the pharmaceutical composition may be used for medical treatment or medical diagnosis as described above.

In yet another aspect of the present invention there is provided an injectable solution comprising the aqueous dispersion of surface-modified heavy metal nanoparticles or pharmaceutical composition comprising the same as described above. In some embodiments, there is provided a sterile syringe comprising the solution. The syringe may be for example disposable and thus used once or manufactured for a multi use routine.

In yet another aspect of the preset invention there is provided a kit which may comprise aqueous dispersion of surface-modified heavy metal nanoparticles dispersed in water or in an aqueous solution. In some embodiments, the aqueous solution comprises a buffer at pH values of between 4.5 and 8; for example, at physiological pH values of about 7.3 to 7.4, or pharmaceutical composition comprising the same means for administering the aqueous dispersion or composition into a patient; and instructions to use.

In another aspect of the present invention, it is provided a kit which may comprise surface-modified heavy metal nanoparticle in a dry form, an aqueous solution for dispersing the surface-modified heavy metal nanoparticle. In some embodiments, the aqueous dispersion comprises water or a buffer at pH values of between 4.5 and 8, for example, at physiological pH values of about 7.3 to 7.4, means for administering the aqueous dispersion into a patient; and instructions for use.

The aqueous solution dispersing the surface-modified heavy metal nanoparticle or the pharmaceutical composition comprising the same may include additional components as long as the components are compatible with the dispersion, wherein compatible is to be understood as for example components which do not cause precipitation or do not cause aggregation.

It should be appreciated that the advantageous stability of the surface-modified heavy metal nanoparticles dispersions and compositions prepared by the methods of preparation disclosed herein and used in the treatment methods disclosed herein provide means and possibility to maintain the surface-modified heavy metal nanoparticles in an aqueous dispersion for extended periods of time or alternatively, in a dry form.

Accordingly, the kits disclosed herein may comprise the aqueous dispersion of the heavy metal nanoparticles and means for administering the same, for example a sterile syringe. In an alternative embodiment the sterile syringe may integrally comprise the pharmaceutical composition comprising the aqueous dispersion of the heavy metal nanoparticles in a ready-to-use form.

The kit of the invention may comprise the surface-modified heavy metal nanoparticles in a dry form for example in a bottle, vial or ampoule, and an aqueous solution for dispersing them and thus in situ preparing an aqueous dispersions in either water or in a buffer solution at pH values of between 4.5 and 8; preferably at physiological pH values of about 7.3 to 7.4, means for injection of the composition such as a sterile syringe.

The kit may comprise a sterile syringe which may comprise surface-modified heavy metal nanoparticles in a dry form which upon usage are to be dispersed and thus preparing an aqueous dispersion of the nanoparticles in either water or in a buffer solution at pH values of, for example, between 4.5 and 8; for example, at physiological pH values of about 7.3 to 7.4, all within the syringe.

The invention further provides a method of treatment or diagnosis of a malignant disorder. The method of the invention comprises administering to a subject in need a therapeutically effective amount of surface-modified heavy metal nanoparticles as described above or of a pharmaceutically composition comprising the same. It should be appreciated that the method of the invention may optionally use the kits as defined by the invention. The method of treatment or diagnosis may comprise administrating by means of for example oral administration, infusion or injection.

Embodiments of the invention with gold as the heavy metal core of the nanoparticles are presented below, as non-limiting examples of the practice of the invention, which can also employ other metal cores in the nanoparticles compositions and dispersions according to the invention.

As used in the specification and the appended claims and in accordance with long-standing patent Law practice, the singular forms "a" "an" and "the" generally mean "at least one", "one or more", and other plural references unless the context clearly dictates otherwise. Thus, for example "a cell" and "a nanoparticle" include mixture of cells and one or more nanoparticles of the type described.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

EXAMPLES

Material and Methods

Oleic acid—65.0-88.0% (GC) (Aldrich)
Ethanol—Frutarom (absolute—Chemically pure)
$HAuCl_4.3H_2O$—ACS reagent, Sigma Aldrich
Ascorbic acid—Cell culture tested, Sigma Aldrich
N-acetyl cysteine—Sigma grade, Sigma Aldrich.
Cysteine—≥97% (Aldrich), Sigma Aldrich
NaOH—SigmaUltra, Sigma Aldrich
n-Hexane—Chemically pure, Frutarom
EMT-6 cancer cells—mouse mammary carcinoma cell line [Technion, Israel]
DMEM, D-Glucose, FBS, L-Glutamine Solution, Pen-Strep Solution—Biological Industries
Trypsin-EDTA solution—Biological Industries
Aqua regia—Aqua Regia is a mixture of hydrochloric acid and nitric acid usually in a molar ratio of 3:1 respectively.
HCl—TraceSelect, Fluka Analytical
$HNO_3$— TraceSelect, Fluka Analytical Example 1

Preparation of Gold Nanoparticles Coated with N-Acetyl Cysteine (NAC)

A mixture of fatty acids, (3.75 ml, 65% oleic acid, linoleic acid 18%, palmitic acid 16%, NaOH 200 mg, and ethanol (15 ml) were added to 30 ml water (Milli-Q, Millipore) and the solution was allowed to stir for 5 minutes on a magnetic stirrer.

Then, $HAuCl_4$ (50 mg) was added while stirring, resulting in a yellowish solution, followed by 5 ml of 0.05M ascorbic acid which was slowly added to the solution. When reduction of the gold species was completed (as indicated by the color of the solution turns to be red-wine), N-acetyl cysteine (124 mg) was slowly added to the solution. The solution was allowed to stir for 30 min.

The pH was then slowly adjusted to pH=9 using NaOH 2M and the resulting solution was further allowed to stir for at least an hour on a magnetic stirrer.

After that, n-hexane (20 ml) was added, and the solution continued to be stirred on a magnetic stirrer for at least an additional hour.

The pH of the resulting reaction mixture was then adjusted to pH=7 using HCl solution (37%).

The mixture was separated into two phases, an organic phase and an aqueous phase, using a separation funnel. The aqueous phase was evaporated under vacuum to remove traces of organic solvents. The dried powder comprising surface-modified gold nanoparticles was dissolved in 5 ml water (Milli-Q, Millipore), yielding an aqueous dispersion of surface-modified gold nanoparticles. The aqueous dispersion was dialyzed using dialysis tube to remove unwanted products.

Figure 1B:
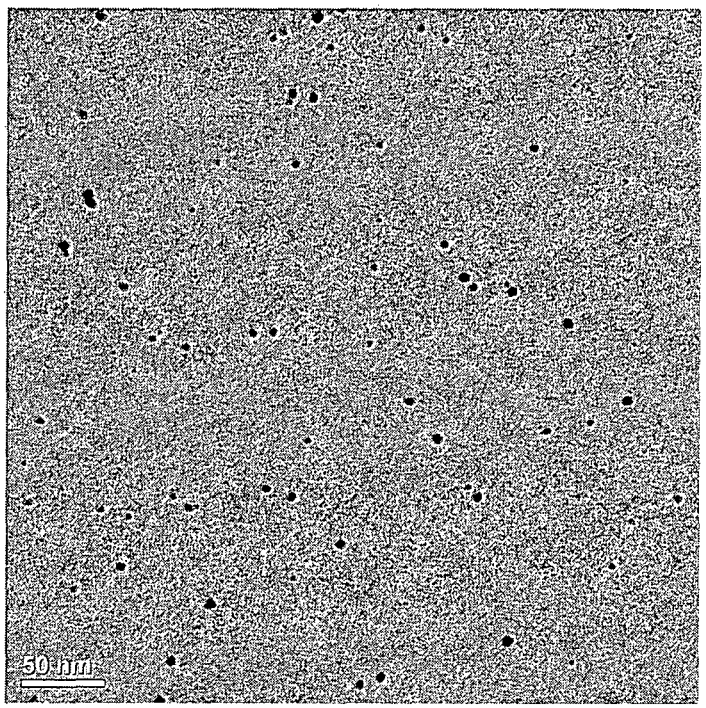

The aqueous dispersions of the surface-modified gold nanoparticles prepared as described herein are present as separate nanoparticles as illustrated in FIGS. 1A and 1B. As shown in FIGS. 1A and 1B, the nanoparticles appearing as black "dots" are separated and do not form aggregates. In addition, as can be seen the gold nanoparticles are present at size equal to or small than 10 nm.

Example 2

Preparation of Gold Nanoparticles Coated with N-Acetyl Cysteine (NAC) and Albumin Oleic acid (3.75 ml), NaOH 200 mg, and ethanol (15 ml) were added to 30 ml of water (Milli-Q, Millipore), the solution was allowed to stir for 5 minutes on a magnetic stirrer.

Then, $HAuCl_4$ (50 mg) was added to give a yellowish solution, while stirring, 5 ml of 0.05 M ascorbic acid was added slowly to the solution. When reduction of the Au is completed (the color of the solution turns to be red-wine) N-acetyl cysteine (111.6 mg in 5 ml water) was added slowly to the solution. The solution was allowed to stir for 30 min.

The pH was then slowly adjusted to pH=9 using NaOH 2M and the resulting solution was allowed to stir for at least one hour on a magnetic stirrer. After that, n-hexane (20 ml) was added, the solution was continued to be stirred on a magnetic stirrer for at least one additional hour.

The pH of the resulting reaction mixture was adjusted to pH=7 using HCl solution (37%).

Then, excess albumin was added and the mixture was allowed to stir for 30 min on the magnetic stirrer.

The mixture was separated into two phases, an organic phase and an aqueous phase using a separation funnel. The aqueous phase was evaporated under vacuum to remove traces of organic solvents. The dried powder comprising surface-modified gold nanoparticles was dissolved in 5 ml water (Milli-Q, Millipore).

Example 3

Preparation of N-Acetyl Cysteine (NAC) and Polyethylene Glycol (PEG) Derivative

Materials and Methods:

Synthetic precursors (N-acetyl-L-cysteine>99%, and p-toluenesulfonic acid monohydrate>98.5%, and Poly (ethylene glycol)-600) were purchased from Sigma-Aldrich without further purification. Solvents (Toluene>99.5%, methyl alcohol "analytical", and dichloromethane "Ar">99.9%) were purchased from Frutarom and Gadot, respectively, and used without further purification. Deuteriated solvents (DMSO-d6 and D2O) for NMR measurements were purchased from Sigma-Aldrich. Solvents for chromatography were analytical grade. Sodium carbonate (Na2CO3) >99.8% and sodium sulfate (Na2SO4)>99% were purchased from Frutarom. Analytical thin-layer chromatography (TLC) was performed on silica-gel plates with F-254 indicator, visualized by irradiation with UV light. Column chromatography was carried out using silica-gel (Grace) 0.040-0.063 mm (Merck). $^1$H NMR spectra were recorded on a Bruker Avance 400 (400 MHz $^1$H NMR). Chemical shift values (δ) are reported in ppm (TMS δ=0 ppm for 1H; residual DMSO-d6 δ=2.5 ppm for 1H). The proton spectra are reported as follows δ (multiplicity, coupling constant J, number of protons, moiety). Multiplicities are indicated by s (singlet), t (triplet), m (multiplet), and so on.

Preparation of NAC:PEG Molecule:

A 250 mL, one-necked, round-bottomed flask equipped with a magnetic stirrer, Dean-Stark trap, and a reflux condenser. The flask was charged with N-acetylcysteine, ("NAC", 3.26 g, 20 mmol) and poly(ethylene glycol)-600, ("PEG-600", 12.0 g, 20 mmol)) in toulene (150 mL). p-toluenesulfonic acid monohydrate ("p-TSA", 4.0 g, 21 mmol) was added and the stirred mixture was heated under reflux in an oil bath (about 140° C.) for 2-3 hr (the reaction was monitored by TLC). The mixture was allowed to cool to ambient temperature and two phases were observed. The mixture was neutralized by adding sodium carbonate (2 g) and stirred for 2 hrs (gas was bubbled). The solvent was evaporated under reduced pressure and the residue was dissolved in dichloromethane, the precipitate was filtered, the organic phase was dried over dry sodium sulfate, filtered and concentrated with a rotary evaporator to give a viscous oil.

The product was purified by column chromatography on silica gel, (eluent: CH2Cl2:CH3OH, 95:5). The appropriate fractions were collected and concentrated by a rotary evaporator to give 7.4 g (9.7 mmol, 48.5%) of the product as a yellow viscous oil. $^1$H-NMR (DMSO-d6, 400 MHz) δ: 1.82 (s, 1H, SH), 2.13 (s, 3H, CH3), 3.34-3.60 (m, 56H, PEG-CH2O), 4.13-4.22 (m, 2H, CH2S), J=8.1 Hz, 1H, CH), 5.69 (s, 1H, NH).

Figure 2:
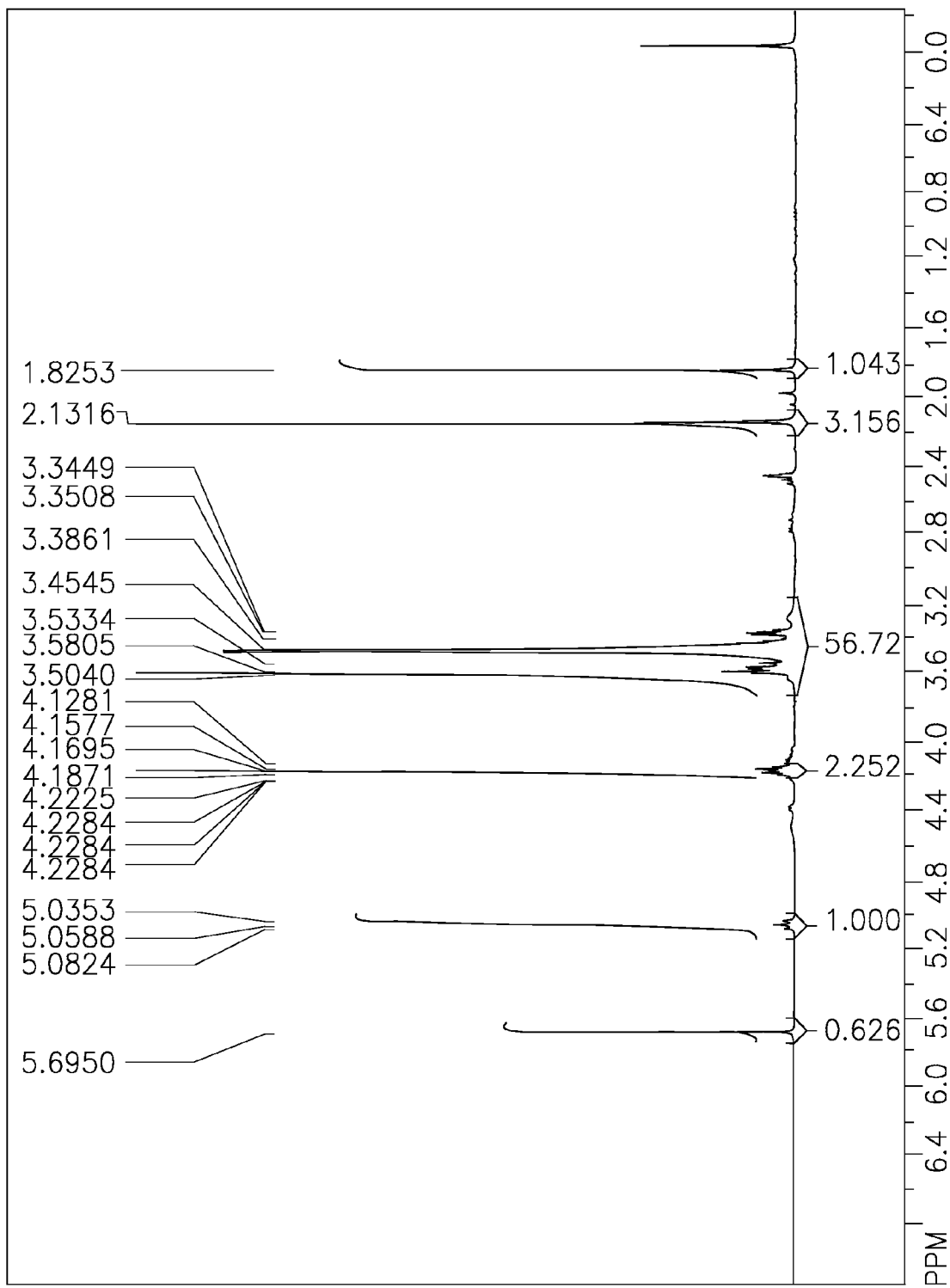
FIG. 2. shows $^1$H-NMR spectrum of PEG-NAC molecule (conjugate/compound) which is used as surface coating for heavy metal nanoparticles.

The $^1$H-NMR Spectrum of NAC-PEG is shown in FIG. 2.

To prepare NAC-PEG coated nanoparticles, 10 mg/ml gold nanoparticles were incubated for 24 hr at 25° C. with PEG-NAC solution (prepared as described above) at a molar ratio of 1:1.

Example 4

Preparation of Gold Nanoparticles Coated with Cysteine

Oleic acid (3.75 ml), NaOH 200 mg, and ethanol (15 ml) are added to 30 ml water (Milli-Q, Millipore) and the solution is allowed to stir for 5 minutes on a magnetic stirrer.

Then, $HAuCl_4$ (50 mg) is added to give a yellowish solution, while stirring, 5 ml of 0.05 M ascorbic acid is added slowly to the solution. When reduction of the Au is completed (the color of the solution turns to be red-wine) cysteine (92.6 mg in 5 ml water) is added slowly to the solution. The solution is allowed to stir for 30 min.

The pH is then slowly adjusted to pH=9 using NaOH 2M and the resulting solution is allowed to stir for at least one hour on a magnetic stirrer. After that, n-hexane (20 ml) is added, the solution is continued to be stirred on a magnetic stirrer for at least one additional hour.

The pH of the resulting reaction mixture is adjusted to pH=7 using HCl solution (37%).

The mixture is separated into two phases, an organic phase and an aqueous phase using a separation funnel. The aqueous phase is evaporated under vacuum to remove traces of organic solvents. The dried powder comprising surface-modified gold nanoparticles is dissolved in 5 ml water (Milli-Q, Millipore).

Example 5

Gold Nanoparticles with a Coat Contains 90% Cysteine and 10% Albumin

Oleic acid (3.75 ml), NaOH 200 mg, and ethanol (15 ml) are added to 30 ml water (Milli-Q, Millipore), the solution is allowed to stir for 5 minutes on a magnetic stirrer.

Then, $HAuCl_4$ (50 mg) is added to give a yellowish solution, while stirring, 5 ml of 0.05 M ascorbic acid is added slowly to the solution. When reduction of the Au is completed (the color of the solution turns to be red-wine) cysteine (83.34 mg in 5 ml water) is added slowly to the solution. The solution is allowed to stir for 30 min.

The pH is then slowly adjusted to pH=9 using NaOH 2M and the resulting solution is allowed to stir for at least one hour on a magnetic stirrer. After that, n-hexane (20 ml) is added, the solution is continued to be stirred on a magnetic stirrer for at least one additional hour.

The pH of the resulting reaction mixture is adjusted to pH=7 using HCl solution (37%).

Then, albumin is added and the mixture is allowed to stir for 30 min on the magnetic stirrer.

The mixture is separated into two phases, an organic phase and an aqueous phase using a separation funnel. The aqueous phase is evaporated under vacuum to remove traces of organic solvents. The dried powder comprising surface-modified gold nanoparticles is dissolved in 5 ml water (Milli-Q, Millipore).

Example 6

Stability of NAC-Surface-Modified Gold Nanoparticles or of PEG-NAC Surface Modified Gold Nanoparticles in Protein Containing Solutions The stability of NAC-surface-modified gold nanoparticles or PEG-NAC-surface-modified gold nanoparticles was tested in growth medium (DMEM). Culture plates were incubated with 9.5 ml of DMEM and 500 μl of NAC-surface-modified gold nanoparticles or PEG-NAC surface-modified gold nanoparticles for 24 hours.

Figure 4:
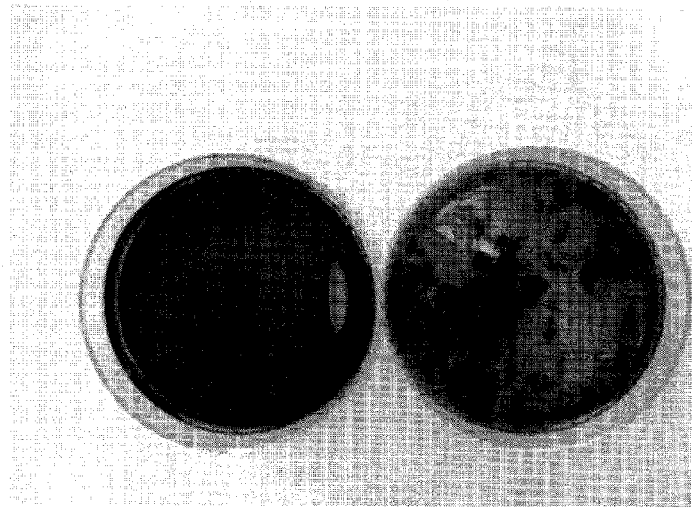
FIG. 4. Pictograms of cell culture medium dish containing PEG-NAC surface coated gold nanoparticles (left hand dish) or cell culture medium dish containing NAC surface coated gold nanoparticles (right hand dish). The cell culture medium dish containing PEG-NAC surface coated gold nanoparticles appears clear as compared to cell culture medium contains the same concentration of NAC surface coated gold nanoparticle, in which, formation of GNPs-protein conjugates is observed.

The results are presented in FIG. 4, which shows pictograms of cell culture medium dish containing PEG-NAC surface coated gold nanoparticles (left hand dish) or cell culture medium dish containing NAC surface coated gold nanoparticles (right hand dish). As shown in FIG. 4, the cell culture medium dish containing PEG-NAC-surface-modified gold nanoparticles appears clear (left hand dish) as compared to cell culture medium contains the same concentration of NAC surface coated gold nanoparticle, in which formation of GNPs-protein conjugates is observed (right hand dish). Thus, the PEG-NAC surface modification provides enhanced solubility and stability to the gold nanoparticles as compared to surface modification by NAC alone.

Likewise, the stability of gold nanoparticles or PEG-NAC surface-modified gold nanoparticles was tested in the following mediums: Blood, growth medium (DMEM) and fetal bovine serum (FBS) solution.

Cultures plates containing 9.5 ml of DMEM or FBS were incubated with 500 μl of gold nanoparticles or PEG-NAC surface-modified gold nanoparticles and tracked for 24 hours. tubes containing 2.5 ml of blood were incubated with 300 μl of gold nanoparticles or PEG-NAC surface-modified gold nanoparticles.

The results show that plates that were incubated with gold nanoparticles, aggregates were formed and black deposits were indentified, which are indicators of unstable nanoparticles. In contrast, plates that were incubated with PEG-NAC surface-modified gold nanoparticles, showed clear solution, with no formation of aggregates or other deposits, indicating that the surface-modified gold nanoparticles are stable in such solutions.

Figure 5A:
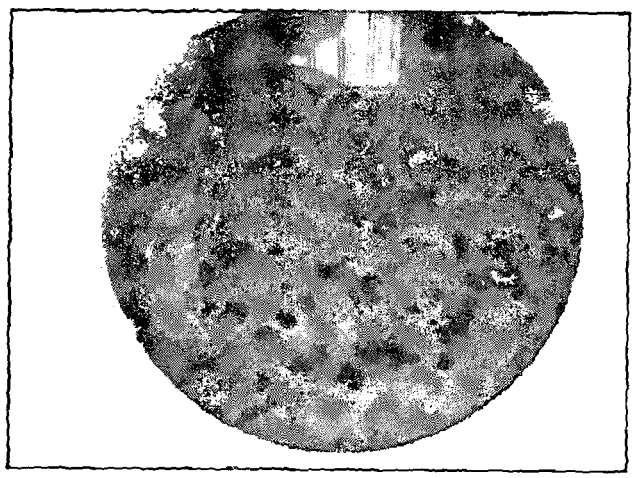
FIG. 5A. Pictogram of NAC-gold nanoparticles in Human blood, formation of protein-GNPs conjugates is shown.
Figure 5B:
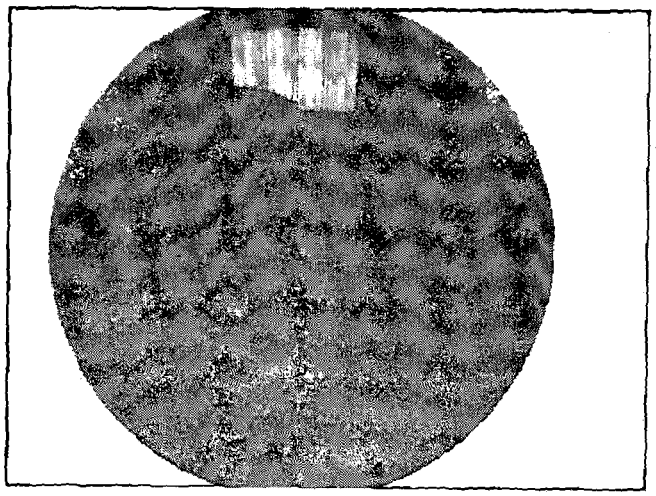
FIG. 5B. Pictogram of PEG-NAC-gold nanoparticles in Human blood. No formation of protein-GNP conjugates is shown.

The results presented in FIGS. 5A-B are of light-microscope images of blood samples incubated with 300 µl of gold nanoparticles or with NAC-PEG surface-modified gold nanoparticles. The results shown in FIGS. 5A-5B demonstrate that whereas in blood incubated with 300 µl of gold nanoparticles, aggregates were formed (FIG. 5A), in blood incubated with 300 µl of PEG-NAC surface-modified gold nanoparticles, no aggregation was detected and the blood solution remained clear (FIG. 5B).

Example 7

In Vitro Assay—Introduction of Gold Nanoparticles to Cancer Cells

EMT-6 cancer cells were grown in Dulbecco's Modified Eagle Medium (DMEM) supplemented with 10% FBS, 2% L-Glutamine Solution (200 mM) and 2% Pen-Strep Solution (Biological Industries) and 4.5 m/1 D-Glucose under regular growth conditions: 5% $CO_2$, and 37.6° C.

An aqueous dispersion of surface-modified gold nanoparticles prepared according to the procedure of Example 1, was added to the cells at one of the final concentrations of 0.02 mg/ml, 0.04 mg/ml. 0.127 mg/ml or 0.253 mg/ml for an incubation periods of 2 hours or 4 hours in the incubator, control cells were kept in the same conditions albeit the addition of gold nanoparticles.

After the incubation times of 2 h or 4 h, cells were washed with PBS, harvested using Trypsin-EDTA solution (Biological Industries), counted under microscope using a microscope counting chamber (Hemocytometer) and digested with aqua regia for ICP (Inductivity Coupled Plasma Spectroscopy) analysis where the threshold value is set to 1 ppb.

Gold concentration in each sample was determined using the Varian 720-ES ICP instrument.

The amount of Au in 1 g cells was calculated. Control groups were also analyzed for gold, the results demonstrated the absence of gold in the control samples.

Determination of gold concentrations following incubation of the cell with aqueous dispersions of surface-modified gold nanoparticles was done using the Varian 720-ES (Inductively coupled plasma mass spectrometry) ICP-MS instrument. ICP-MS is a mass spectrometry instrument that is highly sensitive and capable of determining metal concentration.

As can be seen in Tables 1 and 2, the aqueous dispersions of surface-modified gold nanoparticles are incorporated into the cells at the concentrations and time period tested.

As can be seen in Table 1, incorporation of gold nanoparticles to the cancer cells is dependent on the concentration of the gold nanoparticles in the growth medium, and on the incubation times. There was no toxicity observed in the cells during the incubation of the gold nanoparticles as indicated by comparing the number of the treated cells to the control cells.

In a further study, higher concentrations of gold nanoparticles were used, as can be seen in Table 2, the dependency on the gold nanoparticles concentration and time of incubation is maintained.

More importantly, even at higher concentration no toxic effects on the cells were observed. Therefore, suggesting the safe use of the aqueous dispersions of surface-modified gold nanoparticles in in vivo studies,

TABLE 1

Gold concentrations in cells.

| | Gold concentration in cells medium | |
|---|---|---|
| | 0.02 mg/ml | 0.04 mg/ml |
| Incubation time | Calculated Au(mg)/g in cells | Calculated Au(mg)/g in cells |
| 2 hours-1 | 1.53 | 2.68 |
| 2 hours-2 | 1.72 | 3.05 |
| 4 hours-1 | 2.70 | 4.66 |
| 4 hours-2 | 1.17 | 4.00 |

TABLE 2

Gold concentrations in cells.

| | Gold concentration in cells medium | |
|---|---|---|
| | 0.127 mg/ml | 0.253 mg/ml |
| Incubation time | Calculated Au(mg)/g in cells | Calculated Au(mg)/g in cells |
| 5.5 | 5.19 | 7.12 |
| 0.5 hour-2 | 5.02 | 5.41 |
| 1 hour-1 | 5.99 | 13.2 |
| 1 hour-2 | 5.39 | 17.8 |
| 3 hour-1 | 18 | 32.9 |
| 3 hour-2 | 16.4 | 33.2 |

Example 8

Delivery of Gold Nanoparticles to Tumors and Various Tissues

Balb/C mice (3 groups of 15 mice each) bearing tumors in their thighs (KHJJ line, murine mammary carcinoma) are used in these experiments to show the delivery of gold nanoparticles into tumors and various tissues.

The first experimental group is a control group of mice with an induced tumor, that are injected intravenously (i.v.) with physiological solution (saline). The mice in the second experimental group are injected i.v. with 50 mg/kg of an aqueous dispersion of surface-modified gold nanoparticles prepared according to examples 1 to 4. The mice in the third experimental group are injected i.v. with 50 mg/kg of an aqueous dispersion of surface-modified gold nanoparticles, modified with N-acetyl cysteine and PEG-cysteine.

Tissue samples (kidneys, liver, spleen, lungs, heart and brain) from the different groups are analyzed for the presence of gold using the ICP instrument at 4 hours, 8 hours, 24 hours, 48 hours and 72 hours post-injection.

Example 9

Determination of the PEG-NAC Surface Modified Gold Nanoparticles Maximum Tolerated Dose (MTD)

Mice are repeatedly injected (qd) with increasing doses of aqueous dispersions of PEG-NAC surface-modified gold nanoparticles and are observed for general toxicity signs for a time period of 12-14 days:

I. MTD Assessment Following Multi Dose (IV) Injection

Determination of the MTD (Maximum Tolerated Dose) of gold nanoparticles (GNPs) was assessed following multi dose intravenous (IV) injection to 5 female nude mice, age 8-12 weeks, body weight 18-22 g. Daily dose of 100, 150 and 200 mg/kg, treatment schedule as detailed below. Dosing volume of 10 mL/kg (0.2 mL/20 g mouse). The endpoint of the study was group mean weight loss exceeds 20% or death of >10% of animals in the group. Study Endpoint of 26 days.

The experimental groups were as follows:

Group 1-5 female nude mice injected (i.v.) with 100 mg/kg gold nanoparticles every other day for six days (qod×6).

Group 2-5 female nude mice injected (i.v.) with 100 mg/kg gold nanoparticles for 5 days, two days off and 5 more days (5/2/5).

Group 3-5 female nude mice injected (i.v.) with 150 mg/kg gold nanoparticles for 5 days, two days off and 5 more days (5/2/5).

Group 4-5 female nude mice injected (i.v.) with 200 mg/kg gold nanoparticles for 5 days, two days off and 5 more days (5/2/5).

Figure 3A:
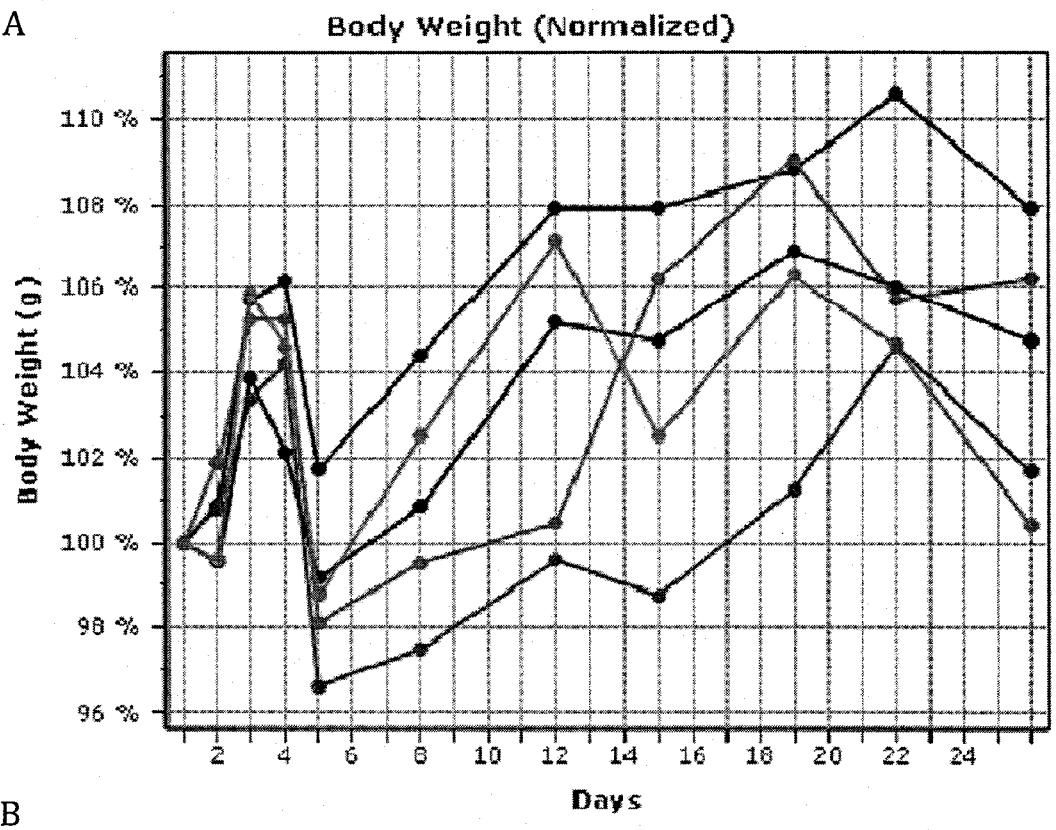
FIGS. 3A-D show graphs of change in mean body weight (g) over time (days after injection) of mice groups following multiple intravenous (IV) injection of varying concentration of gold nanoparticles.
Figure 3B:
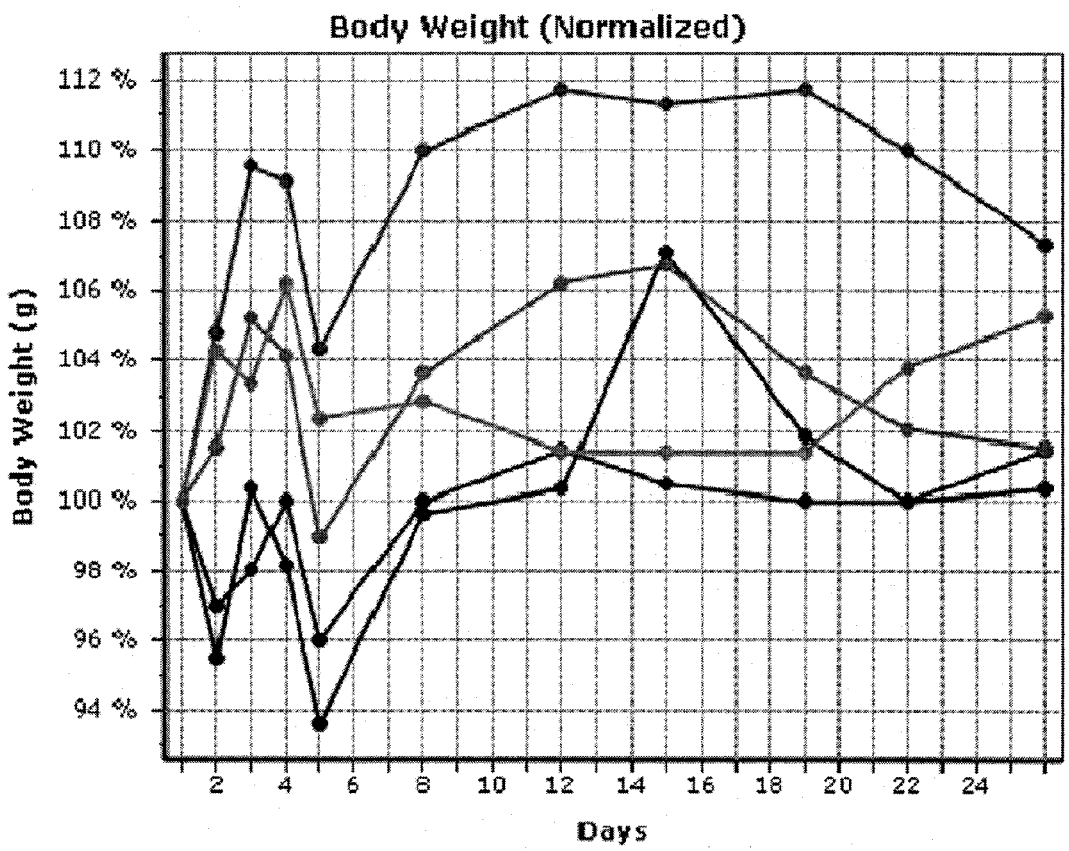
Figure 3C:
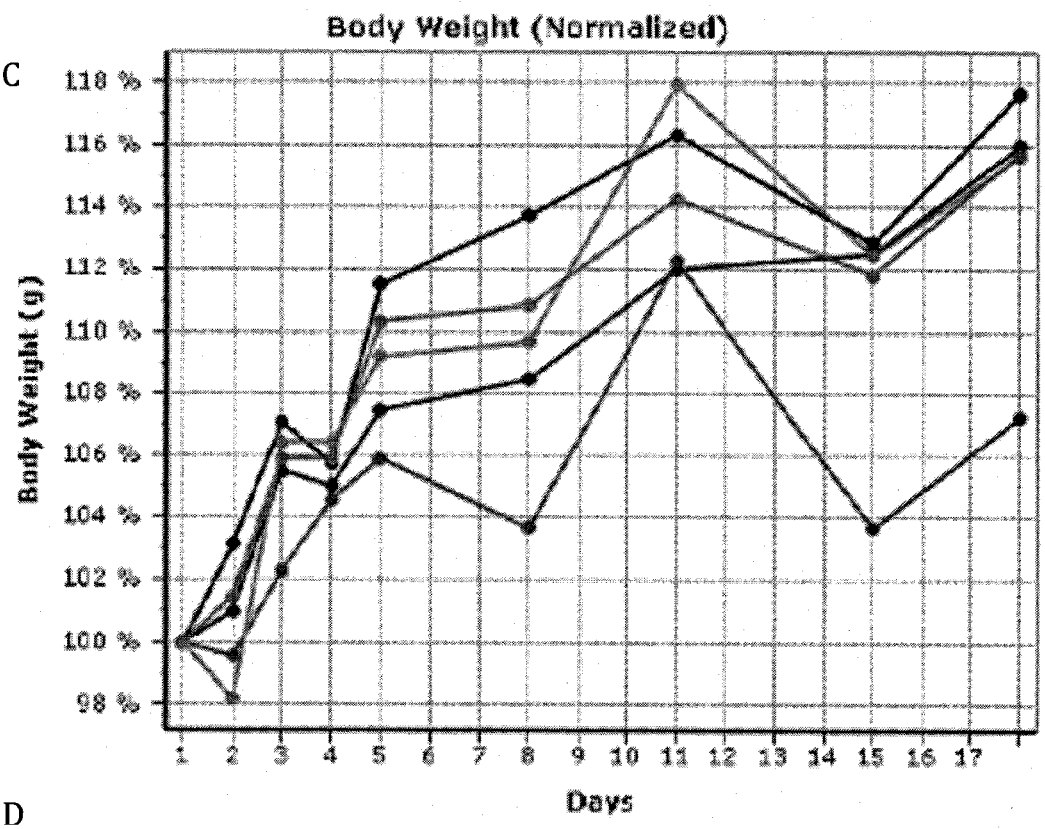
Figure 3D:
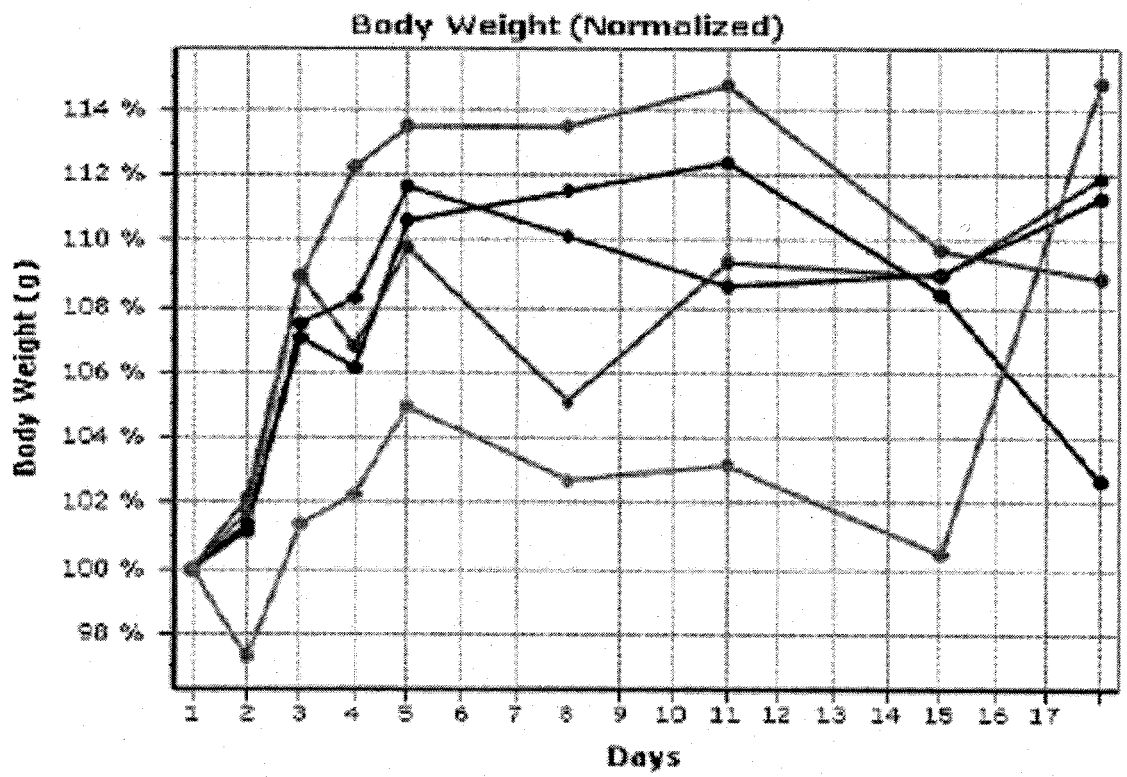

Results:

The results are presented in FIGS. 3A-D, which shows graphs of change in mean body weight (g) over time (days after injection) of the various treated groups. FIG. 3A—change in body weight of group I mice (treated with 100 mg/kg gold nanoparticles every other day, for six days). FIG. 3B—change in body weight of group II mice (treated with 100 mg/kg gold nanoparticles, iv, for five days, two days off and 5 more days (5/2/5)). FIG. 3C—change in body weight of group III mice (treated with 150 mg/kg gold nanoparticles, iv, 5/2/5). FIG. 3D—change in body weight of group IV mice (treated with 200 mg/kg gold nanoparticles, iv, 5/2/5). No mortality occurred in the animals treated with the GNPs prior to the scheduled termination, carried out 26 days post-dosing.

The results demonstrate that no statistically significance loss in mean body weight was confined to any of the GNPs treated groups.

II. MTD Assessment Following Multi Dose (IV) Injection in Combination with Radiation Determination of the MTD (Maximum Tolerated Dose) of Gold nano Particles was assessed following multi dose intravenous (IV) injection to 5 female nude mice (age 8-12 weeks, body weight 18-22 g) in combination with external irradiation.

Figure 3E:
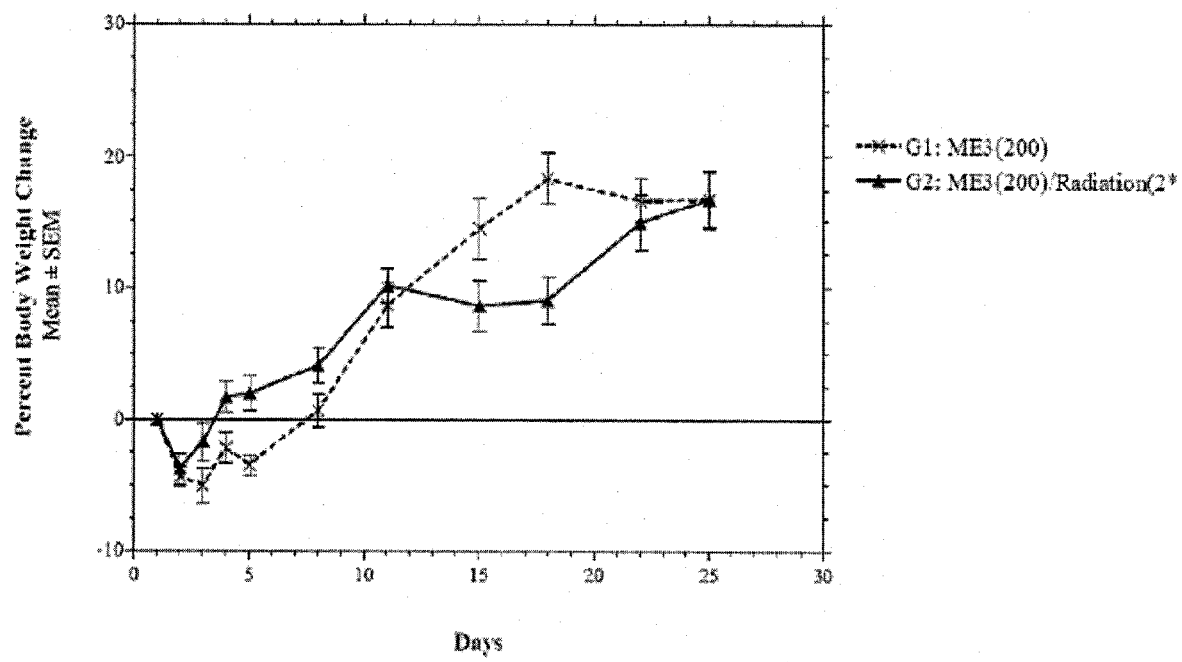
FIG. 3E. A graph of percent body weight changes over time (days) in healthy female nude mice following multi dose i.v. of 200 mg/ml PEG-NAC-gold nanoparticles alone (G1) or in combination with irradiation (G2).

Daily Dose of 100, 150 and 200 mg/kg combined with radiation daily dose of 2 Gy, treatment schedule of 5/2/5. Dosing volume of 10 mL/kg (0.2 mL/20 g mouse). The endpoint of the study was group mean weight loss exceeds 20% or death of >10% of animals in the group. Study Endpoint of 26 days Results:

The results are presented in FIG. 3E, which shows graphs of percent change in body weight (g) over time (days after injection) of group tested with 200 mg/kg of PEG-NAC surface modified gold nanparticles, alone (G1) or in combination with irradiation (G2).

No mortality occurred in the animals treated with the GNPs prior to the scheduled termination, carried out 26 days post-dosing.

No statistically significance loss in mean body weight was confined to any of the GNPs treated groups.

The results indicate that doses of 200 mg/kg and below are safe doses.

Example 10

Toxicity Study

Mice are treated with aqueous dispersions of surface-modified gold nanoparticles and CBC and blood chemistry are determined.

Blood chemistry parameters include: ALKP, amylase, bilirubin, BUN, calcium, cholesterol, ALT, phosphorus ALB, creatine, protein, $NH_3$, AST, Gk, GCT, Glucose, LDH, lipase, magnesium, triglycerides and uric acid.

CBC analysis: Analysis via Forcyte CBC analyzer, samples is measured no more than 4 hours after extraction. Parameters include: measurement of hematocrit (HCT), hemoglobin (HGB), Mean Corpuscular Hemoglobin Concentration (MCHC), Mean Corpuscular Hemoglobin (MCH), Mean Corpuscular Volume (MCV), platelets, Red Blood Cell Count (RBC), and White Blood Cell Count (WBC).

Example 11

Pharmacokinetics (PK) Studies

Collecting tumor and blood samples from animals bearing H460 human Non small cell lung carcinoma (NSCLC), treated with 200 mg/Kg non-surface modified gold nanoparticles or 200 mg/Kg of PEG-NAC surface modified gold nanoparticles.

CR female NCr nu/nu mice, age 8 to 12 weeks were injected with $1\times10^7$ H460 tumor cells sc in flank. Cell injection volume is 0.2 mL/mouse. When tumors reach an average size of 250-350 mg, pair match were done and treatment started. PEG-NAC surface modified gold nanoparticles were injected to group 1 mice and PEG-NAC composition was injected to the second group at a dosing volume of 10 mL/kg (0.200 mL/20 g mouse). Volume was adjusted according to the body weight. Gold nanoparticles dose was 200 mg/Kg.

Figure 6A:
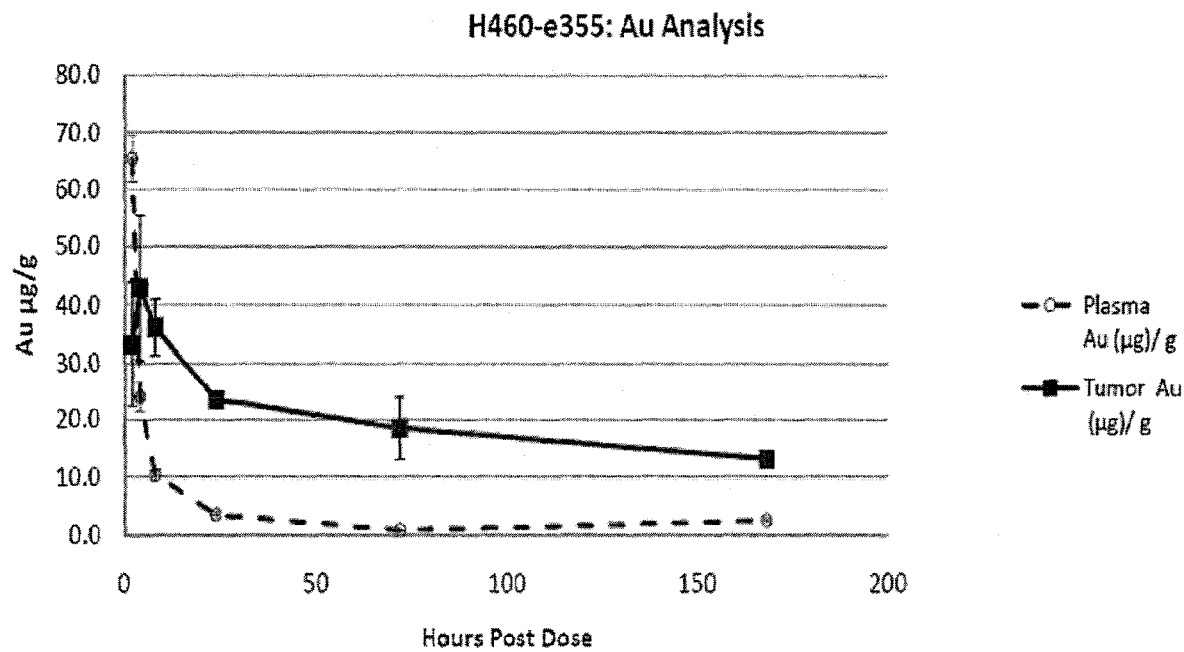
FIG. 6A. A graph showing the pharmacokinetics of NAC surface-modified gold nanoparticles in plasma or in tumors of mice bearing tumors. The graph shows the concentration of gold in plasma or in tumor of mice that were injected with the NAC surface-modified gold nanoparticles (hours after injection).
Figure 6B:
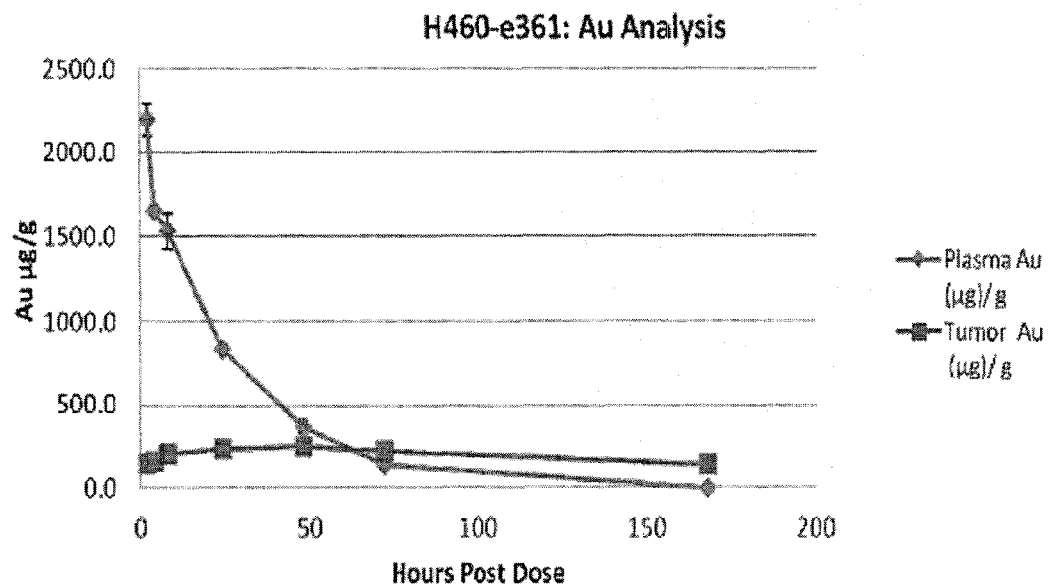
FIG. 6B. A graph showing the pharmacokinetics of PEG-NAC surface-modified gold nanoparticles in plasma or in tumors of mice bearing tumors. The graph shows the concentration of gold in plasma or in tumor of mice bearing tumors that were injected with the PEG-NAC surface-modified gold nanoparticles (hours after injection)

The results are presented in FIGS. 6A-D. FIG. 6A is a graph showing the pharmacokinetics of NAC surface-modified gold nanoparticles in plasma or in tumors of mice bearing tumors. The graph shows the concentration of gold in plasma or in tumor of mice that were injected with the NAC surface-modified gold nanoparticles (hours after injection). FIG. 6B is a graph showing the pharmacokinetics of PEG-NAC surface-modified gold nanoparticles in plasma or in tumors of mice bearing tumors. The graph shows the concentration of gold in plasma or in tumor of mice bearing tumors that were injected with the PEG-NAC surface-modified gold nanoparticles (hours after injection).

Figure 6C:
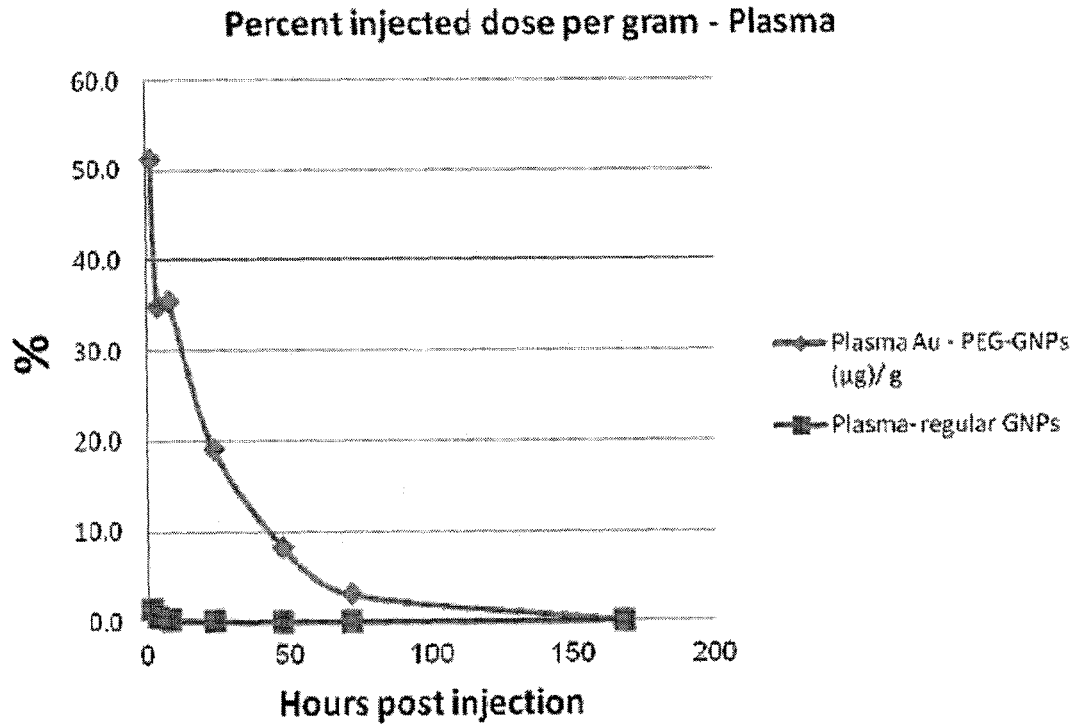
FIG. 6C. A graph showing the percent injected dose (%) per gram tumor over time (days after injection) in tumor, of PEG-NAC surface modified gold nanoparticles (tumor AuPEG-GNPs) or of NAC-surface modified gold nanoparticles ("regular GNPs").
Figure 6D:
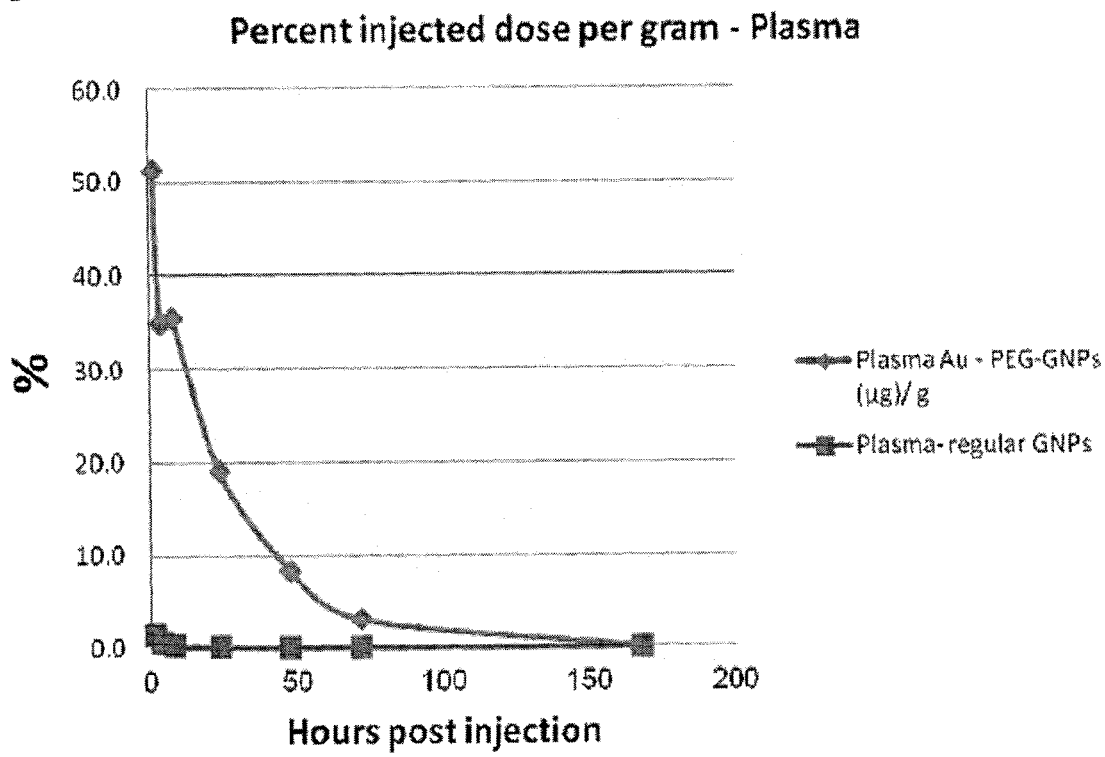
FIG. 6D. A graph showing the percent injected dose (%) per gram over time (days after injection) in plasma, of PEG-NAC surface modified gold nanoparticles (AuPEG-GNPs) or of NAC-surface modified gold nanoparticles ("regular GNPs").

FIGS. 6C-D, shows the percent injected dose per gram tumor or per gram plasma, respectively. FIG. 6C is a graph showing the percent injected dose (%) per gram tumor over time (days after injection) in tumor, of PEG-NAC surface modified gold nanoparticles (tumor AuPEG-GNPs) or of NAC-surface modified gold nanoparticles ("regular GNPs"). FIG. 6D is a graph showing the percent injected dose (%) per gram over time (days after injection) in plasma, of PEG-NAC surface modified gold nanoparticles (AuPEG-GNPs or of NAC-surface modified gold nanoparticles ("regular GNPs").

The results indicate that higher tumor levels were obtained from the PEG-NAC surface modified gold nanoparticles. For PEG-NAC surface modified gold nanoparticles, gold level maximize at 24-72 hours post the injection of the nanoparticles.

Long circulation time (as determined by half-life at blood) was obtained for the PEG-GNPs.

All together, the results demonstrate that the novel surface modification with PEG-NAC improves pharmacokinetics of gold nanoparticles.

The invention claimed is:

1. A surface-modified heavy metal nanoparticle comprising:
a heavy metal core and a coating layer, the coating layer comprising at least one ligand conjugated to polyethylene glycol (PEG),
wherein the at least one ligand is selected from the group consisting of free N-acetyl cysteine (NAC), albumin, free cysteine, free methionine, free glutathione, amino thiols, thio-carboxylic acids, ammonia, amines, diamines and any combination thereof,
wherein the at least one ligand is bound to the surface of the heavy metal core, and
wherein the surface-modified heavy metal nanoparticle is stable in water for at least about 3 months.

2. The surface-modified heavy metal nanoparticle of claim 1 wherein the ligand is free N-acetyl cysteine (NAC).

3. The surface-modified heavy metal nanoparticle of claim 1, wherein the heavy metal is selected from the group consisting of gold, gold species, silver, platinum, iron, copper, nickel, palladium, iridium, titanium, and lead.

4. The surface-modified heavy metal nanoparticle of claim 1, wherein the heavy metal is a gold species.

5. A process for the preparation of surface-modified heavy metal nanoparticles comprising the steps of:
adding at least one ligand conjugated to poly ethylene glycol (PEG) to a mixture comprising metal nanoparticles, wherein the at least one ligand binds to the surface of the heavy metal nanoparticles core, yielding surface-modified heavy metal nanoparticle, which is stable in water for at least about 3 months, wherein the ligand is selected from the group consisting of free N-acetyl cysteine (NAC), albumin, free cysteine, free methionine, free glutathione, amino thiols, thio-carboxylic acids, ammonia, amines, diamines and any combination thereof.

6. The process of claim 5, wherein the ligand is free N-acetyl cysteine (NAC).

7. The process of claim 5, wherein the mixture is prepared by:
(a) mixing at least one surfactant, comprising at least one fatty acid, with at least one organic solvent in a water solution to yield an emulsion;
(b) adding to the emulsion of step (a) a solution of heavy metal species and at least one reducing agent, to yield reduced metal nanoparticles.

8. The process of claim 5, further comprising separating the inorganic phase which contains the surface-modified heavy metal nanoparticles from the organic phase.

9. The process of claim 5, wherein the heavy metal is a gold species.

10. The process of claim 9, wherein the gold species is obtained from $AuCl_3$, $AuF_3$, $AuBr_3$, $HAuCl_4$ or $MAuCl_4$, wherein M represents an alkali metal cation.

11. The process of claim 7, further comprising adding at least one second organic solvent, selected Thorn the group consisting of hexane, cyclohexane, chloroform, diethyl ether, ethyl acetate and toluene.

12. A surface-modified heavy metal nanoparticle obtainable by the process according to claim 5.

13. A pharmaceutical or diagnostic composition comprising surface-modified heavy metal nanoparticles according to claim 1.

14. A method of treatment or diagnosis of a malignant disorder or a cell proliferative disorder comprising the steps of administrating a subject in need a therapeutically effective amount of surface-modified heavy metal nanoparticles as defined in claim 1 or of a pharmaceutically composition comprising the same.

15. The method of claim 14, wherein the malignant disorder is selected from the group consisting of carcinoma, sarcoma, germ cell tumors and blastoma.

16. An N-acetyl cysteine (NAC)-polyethylene glycol (PEG) conjugate for use in surface modification of metal nanoparticles, wherein the N-acetyl cysteine (NAC) is capable of bounding to the surface of the metal nanoparticle core and wherein the NAC-PEG conjugate provides stability to the metal nanoparticles in water for at least about 3 months.

17. The surface-modified heavy metal nanoparticle of claim 2, wherein the free N-acetyl cysteine (NAC) is covalently bound to the surface of the heavy metal nanoparticle core.

18. The surface-modified heavy metal nanoparticle of claim 2, wherein the free N-acetyl cysteine (NAC) is non-covalently bound to the surface of the heavy metal nanoparticle core.

19. The surface-modified heavy metal nanoparticle of claim 2, wherein the binding of the free N-acetyl cysteine (NAC) is via an interaction of a thiol group of the NAC and the metal atoms.

20. The surface-modified heavy metal nanoparticle of claim 1, wherein the ligand is reacted with PEG to produce a ligand-PEG molecule prior to the use of the molecule as the coating layer.

21. The surface-modified heavy metal nanoparticle of claim 1, wherein the nanoparticle is configured to preserve the nano size thereof in water for at least about 3 months.

22. The surface-modified heavy metal nanoparticle of claim 1, wherein the nanoparticle is stable in blood for at least about 24 hours.

* * * * *